(12) United States Patent
Morris et al.

(10) Patent No.: US 9,751,865 B2
(45) Date of Patent: Sep. 5, 2017

(54) DIHYDRO-HYDANTOIN DERIVATIVES WITH HERBICIDAL ACTIVITY

(71) Applicants: SYNGENTA PARTICIPATIONS AG, Basel (CH); SYNGENTA LIMITED, Guildford, Surrey (GB)

(72) Inventors: James Alan Morris, Bracknell (GB); Ravindra Sonawane, Ilhas (IN); Mangala Phadte, Ilhas (IN); Jake Goodwin-Tindall, Bracknell (GB); Jutta Elisabeth Boehmer, Bracknell (GB); Timothy Robert Desson, Bracknell (GB); Claire Janet Russell, Bracknell (GB); Alan Joseph Hennessy, Bracknell (GB); Matthew Brian Hotson, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 0 days.

(21) Appl. No.: 15/107,777

(22) PCT Filed: Dec. 17, 2014

(86) PCT No.: PCT/EP2014/078280
§ 371 (c)(1),
(2) Date: Jun. 23, 2016

(87) PCT Pub. No.: WO2015/097043
PCT Pub. Date: Jul. 2, 2015

(65) Prior Publication Data
US 2016/0318906 A1    Nov. 3, 2016

(30) Foreign Application Priority Data

Dec. 23, 2013 (IN) .......................... 3737/DEL/2013

(51) Int. Cl.
| C07D 403/04 | (2006.01) |
| C07D 487/04 | (2006.01) |
| A01N 43/56 | (2006.01) |
| A01N 43/90 | (2006.01) |

(52) U.S. Cl.
CPC ........... C07D 403/04 (2013.01); A01N 43/56 (2013.01); A01N 43/90 (2013.01); C07D 487/04 (2013.01)

(58) Field of Classification Search
CPC .... C07D 403/04; C07D 487/04; A01N 43/90; A01N 43/56
See application file for complete search history.

(56) References Cited

U.S. PATENT DOCUMENTS

| 3,901,904 A | 8/1975 | Krenzer |
| 4,600,430 A | 7/1986 | Abdulla et al. |
| 4,604,127 A * | 8/1986 | Abdulla ................. A01N 43/58 504/237 |

FOREIGN PATENT DOCUMENTS

| EP | 0136754 A1 | 9/1984 |
| EP | 0205067 A2 | 12/1986 |
| EP | 0801068 A1 | 12/1995 |
| FR | 2450257 A1 | 9/1980 |
| FR | 2543552 A1 | 10/1984 |
| GB | 1555619 A | 11/1979 |
| WO | 9842698 A1 | 10/1998 |
| WO | 0202532 A1 | 1/2002 |

OTHER PUBLICATIONS

International Search report mailed Mar. 11, 2015 in Inter. App. No. PCT/RP2014/078280, mailed Dec. 17, 2015.

* cited by examiner

*Primary Examiner* — John Pak
*Assistant Examiner* — Nathan W Schlientz
(74) *Attorney, Agent, or Firm* — James Cueva

(57) ABSTRACT

The invention relates to substituted dihydro-hydantoin derivatives of the formula (I) wherein X, $R^a$, $R^b$, $R^c$, $R^1$, $R^2$ and $R^3$ are as defined in the specification. Furthermore, the present invention relates to processes and intermediates for making compounds of formula (I), to herbicidal compositions comprising these compounds and to methods of using these compounds 10 to control or inhibit plant growth.

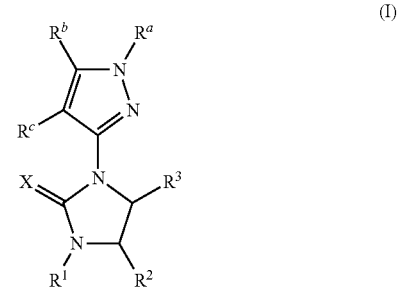

(I)

14 Claims, No Drawings

DIHYDRO-HYDANTOIN DERIVATIVES WITH HERBICIDAL ACTIVITY

RELATED APPLICATION INFORMATION

This application is a 371 national stage entry of International Application No. PCT/EP2014/078280, filed Dec. 17, 2014, which claims priority to IN Application number 3737/DEL/2013, filed Dec. 23, 2013, the contents of which are incorporated herein by reference herein.

The present invention relates to certain substituted dihydro-hydantoin derivatives, to processes for their preparation, herbicidal compositions comprising them, and their use in controlling plants or inhibiting plant growth.

Herbicidal dihydro-hydantoins of the formula

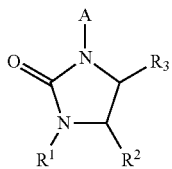

wherein A is a pyridine ring are taught in U.S. Pat. No. 4,600,430. Similar compounds wherein A is a pyridazine ring are taught in U.S. Pat. No. 4,604,127. A number of patent families teach dihydro-hydantoins of the above formula wherein A is a thiadiazole ring (for example U.S. Pat. No. 3,964,895) or an isoxazole ring (for example U.S. Pat. No. 4,302,239).

SUMMARY OF THE INVENTION

In a first aspect, the invention provides compounds of the formula (I)

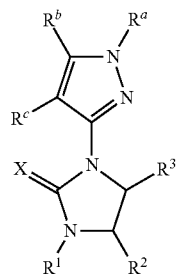

wherein
X is selected from S and O;
$R^a$ is selected from hydrogen, $C_1$-$C_6$ alkyl and $C_1$-$C_6$ haloalkyl;
$R^b$ is selected from hydrogen, formyl, hydroxyl, halogen, nitro, cyano, $C_1$-$C_6$ alkyl, $C_1$-$C_6$ cyanoalkyl, $C_3$-$C_6$ cycloalkyl, $C_3$-$C_6$ cyanocycloalkyl, $C_1$-$C_6$ haloalkyl, $C_1$-$C_6$ alkylthio, $C_1$-$C_6$ alkoxy, $C_1$-$C_6$ alkoxy $C_1$-$C_6$ alkyl, $C_1$-$C_6$ alkthio $C_1$-$C_6$ alkyl, $C_1$-$C_6$ cyanoalkoxy, $C_1$-$C_6$ haloalkoxy, $C_1$-$C_6$ alkoxy $C_1$-$C_6$ alkoxy, $C_2$-$C_6$ alkenyl, $C_2$-$C_6$ alkynyl, $C_2$-$C_6$ cyanoalkenyl, $C_2$-$C_6$ cyanoalkynyl, $C_2$-$C_6$ alkenyloxy, $C_2$-$C_6$ alkynyloxy, $C_2$-$C_6$ haloalkenyl, $C_2$-$C_6$ haloalkynyl, $C_2$-$C_6$ haloalkenyloxy, $C_2$-$C_6$ haloalkynyloxy, $C_1$-$C_6$ alkoxy $C_2$-$C_6$ alkenyl, $C_1$-$C_6$ alkoxy $C_2$-$C_6$ alkynyl, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylsulfonyloxy, $C_1$-$C_6$ alkylcarbonyl, $C_1$-$C_6$ haloalkylcarbonyl, $C_2$-$C_6$ alkenylcarbonyl, $C_2$-$C_6$ alkynylcarbonyl, $C_2$-$C_6$ haloalkenylcarbonyl, $C_2$-$C_6$ haloalkynylcarbonyl, tri $C_1$-$C_6$ alkylsilyl $C_2$-$C_6$ alkynyl, a group $R^5R^6N$—, a group $R^5C(O)N(R^6)$—, a group $R^5R^6NC(O)$—, a group $R^5S(O_2)N(R^6)$—, a group $R^5R^6NSO_2$—, a $C_6$-$C_{10}$ aryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ aryloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ benzyl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ benzyloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_3$-$C_6$ heterocyclyl group optionally substituted by from 1 to 3 groups independently selected from $C_1$-$C_4$ alkyl and a $C_3$-$C_6$ cycloalkyl group optionally substituted with from 1 to 3 groups independently selected from halogen or $C_1$-$C_6$ alkyl;

$R^c$ is selected from hydrogen, halogen, cyano, $C_1$-$C_6$ alkyl and $C_1$-$C_6$ haloalkyl;
or $R^a$ and $R^b$ together with the nitrogen and carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl;
or $R^b$ and $R^c$ together with the carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl;

$R^1$ is selected from hydrogen, $C_1$-$C_4$ alkyl, $C_1$-$C_4$ alkoxy and $C_1$-$C_4$ haloalkyl;
$R^2$ is selected from hydrogen, hydroxyl, $C_1$-$C_4$ alkyl, $C_1$-$C_4$ alkoxy, $C_1$-$C_4$ alkoxy-$C_1$-$C_4$ alkyl, $C_1$-$C_4$ haloalkyl, $C_1$-$C_3$ haloalkoxy and $C_1$-$C_4$ cyanoalkyl;
or $R^1$ and $R^2$ together with the nitrogen and carbon atoms to which they are attached form a 3-7 membered saturated or partially unsaturated ring optionally comprising from 1 to 3 heteroatoms independently selected from S, O and N and optionally substituted with from 1 to 3 groups independently selected from hydroxyl, =O, $C_1$-$C_6$ alkyl or $C_1$-$C_6$ haloalkyl;
$R^3$ is selected from halogen, hydroxyl, —$NR^{10}R^{11}$ or any one of the following groups

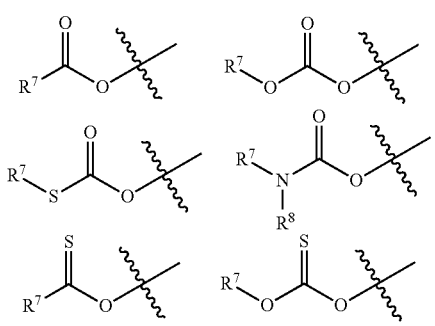

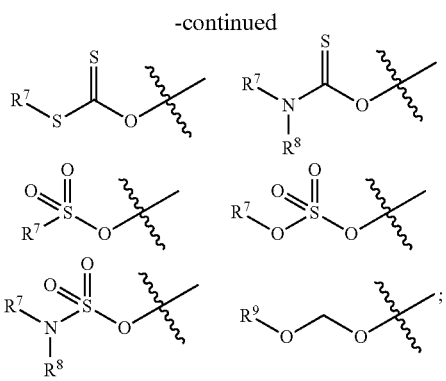

$R^5$ and $R^6$ are independently selected from hydrogen, $C_1$-$C_6$ alkyl, $C_1$-$C_6$ haloalkyl, $C_2$-$C_6$ alkenyl and $C_2$-$C_6$ alkynyl, or $R^5$ and $R^6$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen and $C_1$-$C_6$ alkyl;

$R^7$ and $R^8$ are independently selected from hydrogen, $C_1$-$C_6$ alkyl, $C_1$-$C_6$ haloalkyl, $C_2$-$C_6$ alkenyl, $C_2$-$C_6$ alkynyl, a $C_5$-$C_{10}$ heteroaryl group which can be mono- or bicyclic comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy and a $C_6$-$C_{10}$ aryl group optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, or $R^7$ and $R^8$ together with the atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;

$R^9$ is selected from $C_1$-$C_6$ alkyl and benzyl optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy;

$R^{10}$ and $R^{11}$ are, independently, selected from hydrogen, $C_1$-$C_{20}$ alkyl, $C_1$-$C_{20}$ haloalkyl, $C_2$-$C_{20}$ alkenyl and $C_2$-$C_{20}$ alkynyl, or $R^5$ and $R^6$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen and $C_1$-$C_6$ alkyl;

or an N-oxide or salt form thereof.

In a second aspect, the invention provides herbicidal compositions comprising a compound of the invention together with at least one agriculturally acceptable adjuvant or diluent.

In a third aspect, the invention provides the use of a compound or a composition of the invention for use as a herbicide.

In a fourth aspect, the invention provides a method of controlling weeds in crops of useful plants, comprising applying to said weeds or to the locus of said weeds, or to said useful crop plants, a compound or a composition of the invention.

In a fifth aspect, the invention relates to processes useful in the preparation of compounds of the invention.

In a sixth aspect, the invention relates to intermediates useful in the preparation of compounds of the invention.

DETAILED DESCRIPTION

In particularly preferred embodiments of the invention, the preferred groups for X, $R^a$, $R^b$, $R^c$, $R^1$, $R^2$ and $R^3$, in any combination thereof, are as set out below.

Preferably, X is O.

Preferably, $R^a$ is selected from hydrogen, methyl and ethyl or $R^a$ and $R^b$ together with the nitrogen and carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl. Most preferably, $R^a$ is methyl.

Preferably, $R^b$ is selected from hydrogen, halogen, $C_1$-$C_6$ alkyl, $C_3$-$C_6$ cycloalkyl, $C_1$-$C_6$ haloalkyl, $C_2$-$C_6$ alkenyl, a $C_6$-$C_{10}$ aryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy and a $C_3$-$C_6$ heteroaryl group optionally substituted by from 1 to 3 groups independently selected from $C_1$-$C_4$ alkyl, or $R^a$ and $R^b$ together with the nitrogen and carbon atoms to which they are attached form a 3-7 membered saturated or partially unsaturated ring optionally comprising 1 to 3 heteroatoms independently selected from S, O and N and optionally substituted with 1 to 3 groups independently selected from $C_1$-$C_6$ alkyl or $R^b$ and $R^c$ together with the carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl. More preferably, $R^b$ is selected from hydrogen, halogen, $C_1$-$C_4$ alkyl, $C_1$-$C_4$ haloalkyl, $C_2$-$C_4$ alkenyl and $C_1$-$C_4$ alkoxy. Even more preferably, $R^b$ is selected from $C_1$-$C_4$ alkyl, $C_1$-$C_4$ haloalkyl and $C_1$-$C_4$ alkoxy. Even more preferably $R^b$ is selected from iso-propyl, tert-butyl, fluoromethyl, difluoromethyl, trifluoromethyl and methoxy iso-propyl. Most preferably, $R^b$ is selected from tert-butyl and trifluoromethyl.

Preferably, $R^c$ is selected from hydrogen, methyl and cyano or $R^b$ and $R^c$ together with the carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl. Most preferably, $R^c$ is hydrogen.

Where $R^a$ and $R^b$ or $R^b$ and $R^c$ form a ring structure, the ring may be as described above or, preferably, $R^a$ and $R^b$ or $R^b$ and $R^c$, together with the nitrogen and carbon atoms to which they are attached form a 5-membered saturated ring optionally substituted with from 1 to 3 groups independently selected from $C_1$-$C_3$ alkyl.

In a preferred embodiment, the pyrazole ring is 5-tert-butyl-1-methyl-pyrazol-3-yl.

In a preferred embodiment, the pyrazole ring is 5-isopropyl-1-methyl-pyrazol-3-yl.

In a preferred embodiment, the pyrazole ring is 1-methyl-5-(trifluoromethyl)pyrazol-3-yl.

In a preferred embodiment, the pyrazole ring is 5-tert-butyl-1H-pyrazol-3-yl.

In a preferred embodiment, the pyrazole ring is 5-isopropyl-1H-pyrazol-3-yl.

In a preferred embodiment, the pyrazole ring is 5-(trifluoromethyl)-1H-pyrazol-3-yl.

In a preferred embodiment, the pyrazole ring is 5-(1,1-dimethylbut-3-enyl)-1-methyl-pyrazol-3-yl.

In a preferred embodiment, the pyrazole ring is 4,4-dimethyl-5,6-dihydropyrrolo[1,2-b]pyrazol-2-yl.

In a preferred embodiment, the pyrazole ring is 4,4-dimethyl-6,7-dihydro-5H-pyrazolo[1,5-a]pyridin-2-yl.

Preferably $R^1$ is selected from $C_1$-$C_4$ alkyl, $C_1$-$C_4$ alkoxy and $C_1$-$C_4$ haloalkyl. More preferably, $R^1$ is selected from $C_1$-$C_4$ alkyl and $C_1$-$C_4$ alkoxy. Most preferably, $R^1$ is selected from methyl and methoxy.

Preferably $R^2$ is selected from hydrogen, hydroxyl, $C_1$-$C_3$ alkyl, $C_1$-$C_3$ alkoxy and $C_1$-$C_3$ alkoxy-$C_1$-$C_3$ alkyl. More preferably $R^2$ is selected from hydrogen, methyl, ethoxy and methoxymethyl. Most preferably, $R^2$ is selected from hydrogen, methyl and ethoxy.

Preferably, $R^3$ is selected from hydroxyl, halogen, $C_1$-$C_6$ alkylcarbonyloxy, $C_1$-$C_6$ alkoxycarbonyloxy and aryloxycarbonyloxy wherein the aryl group may be substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy. Even more preferably, $R^3$ is selected from hydroxyl and halogen. Most preferably, $R^3$ is hydroxyl.

In a preferred embodiment, the invention provides compounds of formula (I)

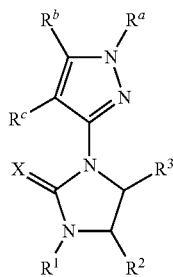

wherein X is O, $R^1$ is selected from hydrogen, $C_1$-$C_3$ alkyl and $C_1$-$C_3$ alkoxy, $R^2$ is selected from hydrogen, hydroxyl, $C_1$-$C_3$ alkyl, $C_1$-$C_3$ alkoxy and $C_1$-$C_3$ alkoxy-$C_1$-$C_3$ alkyl, $R^3$ is hydroxyl, $R^a$ is $C_1$-$C_3$ alkyl, $R^b$ is selected from $C_1$-$C_4$ alkyl, $C_1$-$C_3$ haloalkyl and $C_1$-$C_4$ alkoxy or $R^a$ and $R^b$ together with the nitrogen and carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl and $R^c$ is selected from hydrogen and cyano.

More preferably, X is O, $R^1$ is selected from hydrogen, methyl and methoxy, $R^2$ is selected from hydrogen, hydroxyl, methyl, ethoxy and methoxymethyl, $R^3$ is hydroxyl, $R^a$ is methyl, $R^b$ is selected from iso-propyl, tert-butyl, fluoromethyl, difluoromethyl, trifluoromethyl and methoxy iso-propyl or $R^a$ and $R^b$ together with the nitrogen and carbon atoms to which they are attached form a 5-membered saturated ring optionally substituted with from 1 to 3 groups independently selected from $C_1$-$C_3$ alkyl and $R^c$ is hydrogen.

Most preferably, X is O, $R^1$ is selected from methyl and methoxy, $R^2$ is selected from hydrogen, methyl and ethoxy, $R^3$ is hydroxyl, $R^a$ is methyl, $R^b$ is selected from tert-butyl and trifluoromethyl or $R^a$ and $R^b$ together form the group —$CH_2CH_2C(CH_3)_2$— and $R^c$ is hydrogen.

The compounds of formula (I) may exist as different geometric isomers, or in different tautomeric forms. This invention covers all such isomers and tautomers, and mixtures thereof in all proportions, as well as isotopic forms such as deuterated compounds.

The compounds of this invention may contain one or more asymmetric centers and may thus give rise to optical isomers and diastereomers. While shown without respect to stereochemistry, the present invention includes all such optical isomers and diastereomers as well as the racemic and resolved, enantiomerically pure R and S stereoisomers and other mixtures of the R and S stereoisomers and agrochemically acceptable salts thereof. It is recognized that certain optical isomers, or diastereomers may have favorable properties over the other. Thus when disclosing and claiming the invention, when a racemic mixture is disclosed, it is clearly contemplated that both optical isomers, including diastereomers substantially free of the other are disclosed and claimed as well.

Alkyl, as used herein, refers to an aliphatic hydrocarbon chain and includes straight and branched chains e.g. of 1 to 8 carbon atoms such as methyl, ethyl, n-propyl, isopropyl, n-butyl, isobutyl, sec-butyl, t-butyl, n-pentyl, isopentyl, neopentyl, n-hexyl, and isohexyl.

Alkenyl, as used herein, refers to an aliphatic hydrocarbon chain having at least one double bond, and preferably one double bond, and includes straight and branched chains e.g. of 2 to 8 carbon atoms such as ethenyl (vinyl), prop-1-enyl, prop-2-enyl (allyl), isopropenyl, but-1-enyl, but-2-enyl, but-3-enyl, 2-methypropenyl.

Alkynyl, as used herein, refers to an aliphatic hydrocarbon chain having at least one triple bond, and preferably one triple bond, and includes straight and branched chains e.g. of 2 to 8 carbon atoms such as ethynyl, prop-1-ynyl, prop-2-ynyl (propargyl) but-1-ynyl, but-2-ynyl and but-3-ynyl.

Cycloalkyl, as used herein, refers to a cyclic, saturated hydrocarbon group having from 3 to 6 ring carbon atoms. Examples of cycloalkyl groups are cyclopropyl, cyclobutyl, cyclopentyl and cyclohexyl.

Alkoxy, as used herein, refers to the group —OR, wherein R is alkyl as defined above. Examples of alkoxy groups include methoxy, ethoxy, n-propoxy, isopropoxy, n-butoxy, isobutoxy, sec-butoxy, t-butoxy, n-pentoxy, isopentoxy, neopentoxy, n-hexyloxy, and isohexyloxy.

Alkenyloxy, as used herein, refers to the group —OR, wherein R is alkenyl as defined above. Examples of alkenyloxy groups are ethenyloxy, propenyloxy, isopropenyloxy, but-1-enyloxy, but-2-enyloxy, but-3-enyloxy, 2-methypropenyloxy etc.

Alkynyloxy, as used herein, refers to the group —OR, wherein R is alkynyl is as defined above. Examples of alkynyloxy groups are ethynyloxy, propynyloxy, but-1-ynyloxy, but-2-ynyloxy and but-3-ynyloxy.

Alkoxyalkyl, as used herein, refers to the group —ROR, wherein each R is, independently, an alkyl group as defined above.

Alkoxyalkenyl as used herein refers to the group —ROR', wherein R is an alkyl group as defined above and R' is an alkenyl group as defined above.

Alkoxyalkynyl as used herein refers to the group —ROR', wherein R is an alkyl group as defined above and R' is an alkynyl group as defined above.

Alkoxyalkoxy, as used herein, refers to the group —OROR, wherein each R is, independently, an alkyl group as defined above.

Cyanoalkyl, as used herein, refers to an alkyl group substituted with one or more cyano groups.

Cyanoalkenyl, as used herein, refers to an alkenyl group substituted with one or more cyano groups.

Cyanoalkynyl, as used herein, refers to an alkynyl group substituted with one or more cyano groups.

Cyanocycloalkyl, as used herein, refers to an cycloalkyl group substituted with one or more cyano groups.

Cyanoalkoxy, as used herein, refers to the group —OR, wherein R is cyanoalkyl as defined above.

Halogen, halide and halo, as used herein, refer to iodine, bromine, chlorine and fluorine.

Haloalkyl, as used herein, refers to an alkyl group as defined above wherein at least one hydrogen atom has been replaced with a halogen atom as defined above. Examples of haloalkyl groups include chloromethyl, dichloromethyl, trichloromethyl, fluoromethyl, difluoromethyl and trifluoromethyl. Preferred haloalkyl groups are fluoroalkyl groups {i.e. haloalkyl groups, containing fluorine as the only halogen). More highly preferred haloalkyl groups are perfluoroalkyl groups, i.e. alkyl groups wherein all the hydrogen atoms are replaced with fluorine atoms.

Haloalkenyl, as used herein, refers to an alkenyl group as defined above wherein at least one hydrogen atom has been replaced with a halogen atom as defined above.

Haloalkynyl, as used herein, refers to an alkynyl group as defined above wherein at least one hydrogen atom has been replaced with a halogen atom as defined above.

Haloalkoxy, as used herein, refers to the group —OR, wherein R is haloalkyl as defined above.

Haloalkenyloxy, as used herein, refers to the group —OR, wherein R is haloalkenyl as defined above.

Haloalkynyloxy, as used herein, refers to the group —OR, wherein R is haloalkynyl as defined above.

Alkylthio, as used herein, refers to the group —SR, wherein R is an alkyl group as defined above. Alkylthio groups include, but are not limited to, methylthio, ethylthio, propylthio, tert-butylthio, and the like.

Alkylthioalkyl, as used herein, refers to the group —RSR, wherein each R is, independently, an alkyl group as defined above.

Haloalkylthio, as used herein, refers to the group —SR, wherein R is a haloalkyl group as defined above.

Alkylsulfinyl, as used herein, refers to the group —S(O)R, wherein R is an alkyl group as defined above.

Alkylsulfonyl, as used herein, refers to the group —S(O)$_2$R, wherein R is an alkyl group as defined above.

Haloalkylsulfinyl, as used herein, refers to the group —S(O)R, wherein R is a haloalkyl group as defined above.

Haloalkylsulfonyl, as used herein, refers to the group —S(O)$_2$R, wherein R is a haloalkyl group as defined above.

Alkylsulfonyloxy, as used herein, refers to the group —OSO$_2$R, wherein R is an alkyl group as defined above.

Alkylcarbonyl, as used herein, refers to the group —COR, wherein R is an alkyl group as defined above. Examples of alkylcarbonyl groups include ethanoyl, propanoyl, n-butanoyl, etc.

Alkenylcarbonyl, as used herein, refers to the group —COR, wherein R is an alkenyl group as defined above.

Alkynylcarbonyl, as used herein, refers to the group —COR, wherein R is an alkynyl group as defined above.

Haloalkylcarbonyl, as used herein, refers to the group —COR, wherein R is a haloalkyl group as defined above.

Haloalkenylcarbonyl, as used herein, refers to the group —COR, wherein R is a haloalkenyl group as defined above.

Haloalkynylcarbonyl, as used herein refers to the group —COR, wherein R is a haloalkynyl group as defined above.

Alkycarbonyloxy, as used herein, refers to the group —OC(O)R, wherein R is an alkyl group as defined above.

Alkoxycarbonyloxy, as used herein, refers to the group —OC(O)OR, wherein R is an alkyl group as defined above. Examples of alkoxycarbonyloxy groups are methoxycarbonyloxy, ethoxycarbonyloxy, propoxycarbonyloxy, but-1-oxycarbonyloxy, but-2-oxycarbonyloxy and but-3-oxycarbonyloxy.

Trialkylsilylalkynyl, as used herein, refers to the group —RSi(R')$_3$, wherein R is an alkynyl group as defined above and each R' is, independently, selected from an alkyl group as defined above.

Formyl, as used herein, refers to the group —C(O)H.

Hydroxy or hydroxyl, as used herein, refers to the group —OH.

Nitro, as used herein, refers to the group —NO$_2$.

Cyano, as used herein, refers to the group —CN.

Aryl, as used herein, refers to an unsaturated aromatic carbocyclic group of from 6 to 10 carbon atoms having a single ring (e.g., phenyl) or multiple condensed (fused) rings, at least one of which is aromatic (e.g., indanyl, naphthyl). Preferred aryl groups include phenyl, naphthyl and the like. Most preferably, an aryl group is a phenyl group.

Aryloxy, as used herein, refers to the group —O-aryl, wherein aryl is as defined above. Preferred aryloxy groups include phenoxy, naphthyloxy and the like.

Aryloxycarbonyloxy, as used herein, refers to the group —OC(O)O-aryl wherein aryl is a as defined above.

Benzyl, as used herein, refers to the group —CH$_2$C$_6$H$_5$.

Benzyloxy, as used herein, refers to the group —OCH$_2$C$_6$H$_5$.

Heterocyclyl, as used herein, refers to a non-aromatic ring system containing 3 to 10 ring atoms, at least one ring heteroatom and consisting either of a single ring or of two or more fused rings. Preferably, single rings will contain up to three and bicyclic systems up to four heteroatoms which will preferably be chosen from nitrogen, oxygen and sulfur. Examples of such groups include pyrrolidinyl, imidazolinyl, pyrazolidinyl, piperidyl, piperazinyl, quinuclidinyl, morpholinyl, together with unsaturated or partially unsaturated analogues such as 4,5,6,7-tetrahydro-benzothiophenyl, chromen-4-onyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl, 4,5-dihydro-isoxazolyl, tetrahydrofuranyl and morpholinyl.

Heteroaryl, as used herein, refers to a ring system containing 5 to 10 ring atoms, 1 to 4 ring heteroatoms and consisting either of a single aromatic ring or of two or more fused rings, at least one of which is aromatic. Preferably, single rings will contain up to three and bicyclic systems up to four heteroatoms which will preferably be independently chosen from nitrogen, oxygen and sulfur. Examples of such groups include pyridyl, pyridazinyl, pyrimidinyl, pyrazinyl, triazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. Examples of bicyclic groups are benzothiophenyl, benzimidazolyl, benzothiadiazolyl, quinolinyl, cinnolinyl, quinoxalinyl and pyrazolo[1,5-a]pyrimidinyl.

'Saturated ring', as used herein, refers to a ring system in which the atoms in the ring are linked by single bonds.

'Partially unsaturated ring', as used herein, refers to a ring system in which at least two atoms in the ring are linked by a double bond. Partially unsaturated ring systems do not include aromatic rings.

'Optionally substituted' as used herein means the group referred to can be substituted at one or more positions by any one or any combination of the radicals listed thereafter. For most groups, one or more hydrogen atoms are replaced by the radicals listed thereafter. For halogenated groups, for example, haloalkyl groups, one or more halogen atoms are replaced by the radicals listed thereafter.

Suitable salts include those derived from alkali or alkaline earth metals and those derived from ammonia and amines. Preferred cations include sodium, potassium, magnesium, and ammonium cations of the formula $N^+(R^{19}R^{20}R^{21}R^{22})$ wherein $R^{19}$, $R^{20}$, $R^{21}$ and $R^{22}$ are independently selected from hydrogen, $C_1$-$C_6$ alkyl and $C_1$-$C_6$ hydroxyalkyl. Salts of the compounds of formula (I) can be prepared by treatment of compounds of formula (I) with a metal hydroxide, such as sodium hydroxide, or an amine, such as ammonia, trimethylamine, diethanolamine, 2-methylthiopropylamine, bisallylamine, 2-butoxyethylamine, morpholine, cyclododecylamine, or benzylamine. Amine salts are often preferred forms of the compounds of formula (I) because they are water-soluble and lend themselves to the preparation of desirable aqueous based herbicidal compositions.

Acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety.

In another aspect the present invention provides intermediates useful in the preparation of compounds of the invention.

In one embodiment, there are provided intermediates of the formula (III), wherein X, $R^1$, $R^2$, $R^a$, $R^b$ and $R^c$ are as defined above.

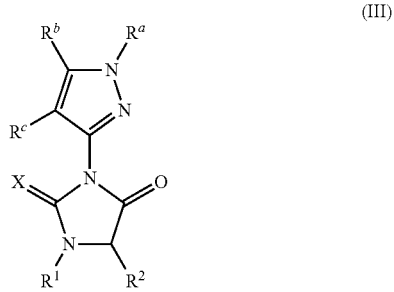

(III)

In another embodiment, there are provided intermediates shown below wherein X, $R^1$, $R^2$, $R^{10}$, $R^{11}$, $R^a$, $R^b$ and $R^c$ are as defined above.

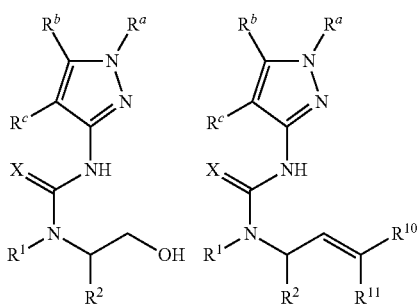

-continued

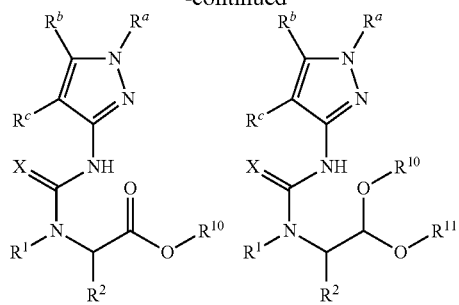

Compounds of the invention may be prepared by techniques known to the person skilled in the art of organic chemistry. General methods for the production of compounds of formula (I) are described below. Unless otherwise stated in the text, the substituents $R^1$, $R^2$, $R^3$, $R^a$, $R^b$ and $R^c$ are as defined hereinbefore. The starting materials used for the preparation of the compounds of the invention may be purchased from usual commercial suppliers or may be prepared by known methods. The starting materials as well as the intermediates may be purified before use in the next step by state of the art methodologies such as chromatography, crystallization, distillation and filtration.

For example, compounds of formula (IX) wherein $R^1$ is an alkyl or alkoxy group and $R^2$ is a hydrogen or alkyl group may be prepared by reaction of amino-pyrazole (IV) with phenylchloroformate to give carbamate product (V). The subsequent reaction with an appropriately substituted amino-ester (VI) gives compounds of type (VII) and subsequent cyclisation gives compounds of type (VIII) and reduction with e.g. with sodium borohydride gives compounds of type (IX). The methyl amino-ester (VI) may also be replaced by other amino esters or amino-acids. Phenyl chloroformate may be replaced by other activating groups such as phosgene or para-nitrophenyl chloroformate. The cyclisation to (VIII) may occur in situ or require heating for carboxylic acids or esters or treatment with a reagent such as thionyl chloride for carboxylic acids. Esters of type (VII) may also be reduced to their corresponding primary alcohols and then such alcohols can be re-oxidised to compounds of type (IX) with oxidants such as Dess-Martin periodinane.

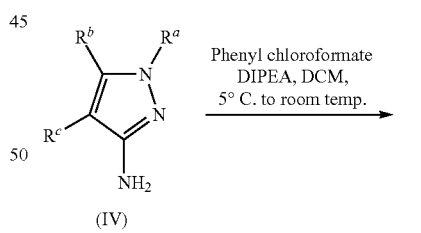

(IV)

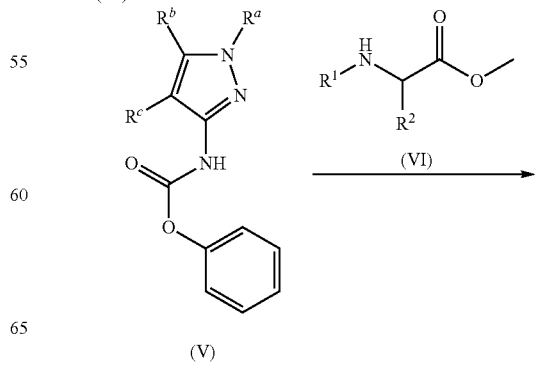

(V)

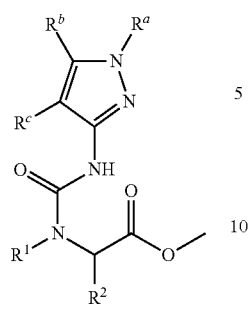

(VII)

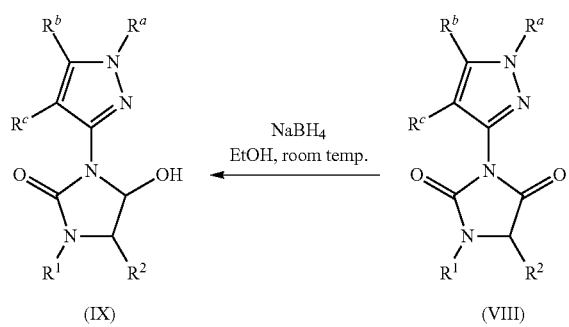

(IX)      (VIII)

Compounds of formula (X) wherein $R^2$ is an hydroxy group may be prepared by the reaction of compounds of type (V) with an appropriate amine (XI) to give urea (XII), which can react with aqueous glyoxal solution to give product (X). Compounds of formula (IX) where $R^2$ is an alkoxy group may be prepared by reacting compounds of formula (X) with alcohols of type $R^4$—OH under acidic conditions.

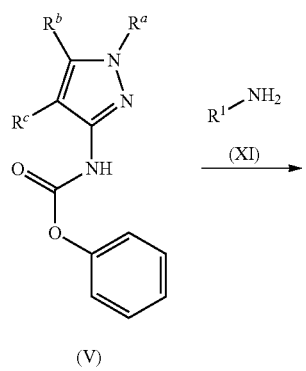

(V)

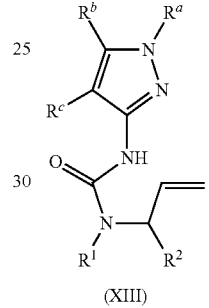

(XI)

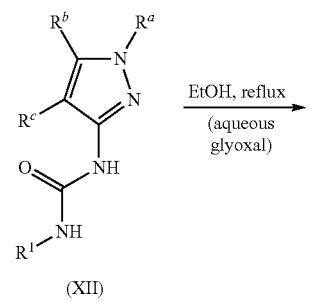

(XII)

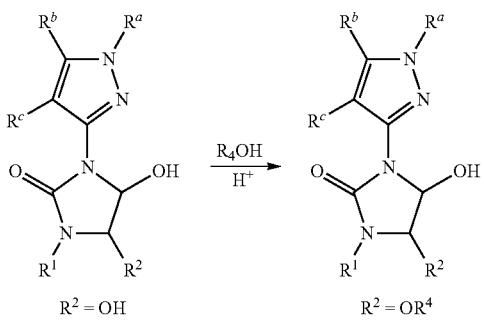

R² = OH          R² = OR⁴
(X)             (IX)

Alternatively oxidative cleavage (using ozonolysis or $OsO_4/NaIO_4$ or similar conditions) of an appropriate vinyl compound such as (XIII) or derivatives thereof and cyclisation could give the desired product.

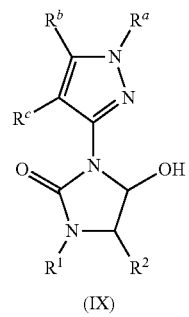

(XIII)

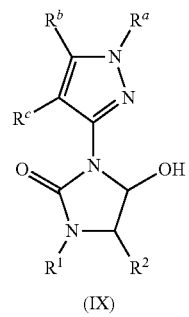

(IX)

Amino-pyrazoles are commercially available or may be made by standard procedures such as those outlined below.

Reaction of hydrazine, or an appropriate salt, with a β-ketonitrile (XIV) in a solvent such as ethanol affords the desired amino pyrazoles (IV) where $R^a$ and $R^c$=H as described in *Journal of Medicinal Chemistry* 2008, vol. 51, No. 15, 4672-4684.

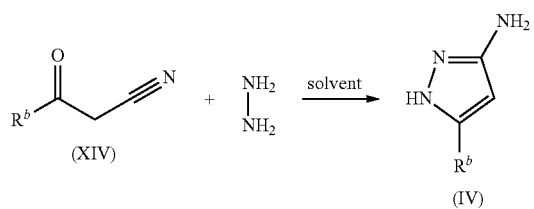

(XIV)                     (IV)

Alternatively, reaction of an alkyl hydrazine, or an appropriate salt, with a nitrile vinyl chloride (XV), or its isomers, in a solvent such as ethanol, with an appropriate base, such as K$_2$CO$_3$, affords the desired amino pyrazoles (IV) and undesired isomer (XVI) as described in *Pharmazie* 1989, vol. 44, No. 8 p. 535-539 or *Journal of Heterocyclic Chemistry* 1982, vol. 19, p. 1267-1273.

appropriate solvent, such as THF, with the relevant alkyl halide, followed by ester hydrolysis affords the pyrazole 3-carboxylic acids (XIX). Reaction of (XIX) with DPPA in a solvent, such as tBuOH, and triethylamine affords a mixture of the urea (XX) and the desired amino pyrazole (IV). (XX) may be further converted into (IV) under hydrolysis conditions.

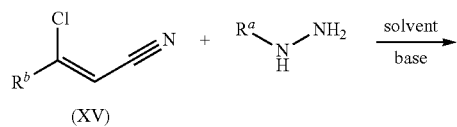

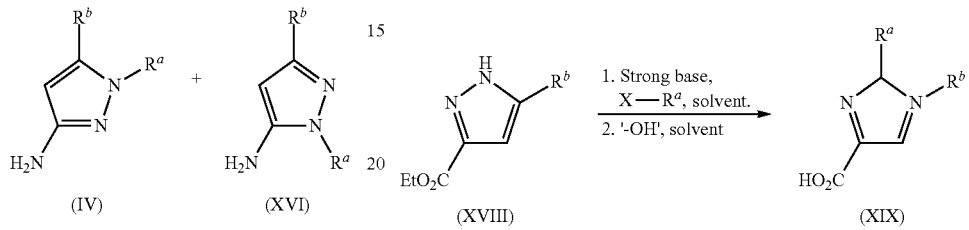

Nitrile vinyl chlorides (XV) can be prepared from the corresponding 3-ketonitrile and a suitable chlorination reagent such as PCl$_5$ or POCl$_3$, in a suitable solvent, such as dichlormethane. Alternatively the nitrile vinyl chlorides (XV) can be prepared from the corresponding ketone.

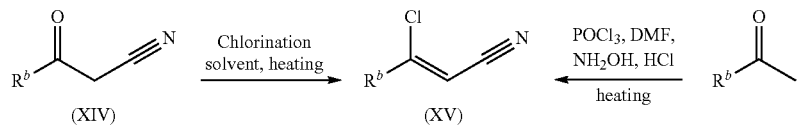

Alternatively nitrile vinyl chlorides of type (XVI) can be prepared from the corresponding aldehyde and phosphonate (XVII), with an appropriate base, such as LiN(TMS)$_2$ in an appropriate solvent, such as THF. Phosphonate (XVII) can be prepared as described in *J. Chem. Soc., Perkin Trans.* 1 2000, 3311-3316.

-continued

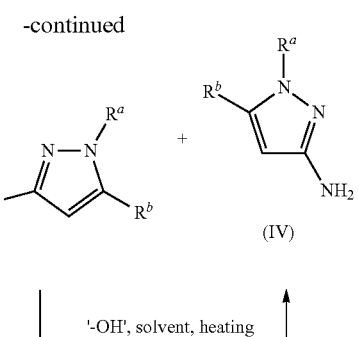

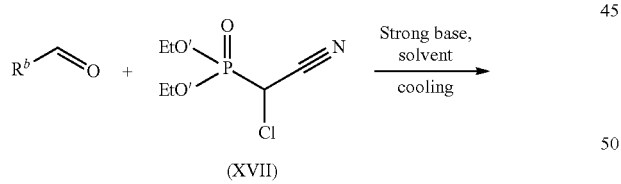

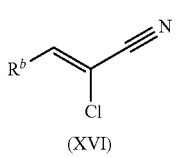

Alternatively the amino pyrazoles can be prepared from the corresponding pyrazole 3-carboxylates (XVIII). N-alkylation employing an appropriate base, such as tBuOK, in the Alternatively deprotonation of pyrazole (XXI) with an appropriate base, such as BuLi, followed by quenching with an electrophile, such as halogens, alkyl halides, aldehydes, ketones etc as described in *Journal of Organic Chemistry* 1984, vol. 49, No. 7 p. 1224-1227, affords (XXII). Deprotection of the pyrrole masked amine (XXII), also described in the above reference, affords the desired amino pyrazoles (IV). Alternatively, further functional group transformations of (XXII), which will be know to those skilled in the art, can be used to further vary the pyrazole 5-position (R$^b$) before deprotection to (IV).

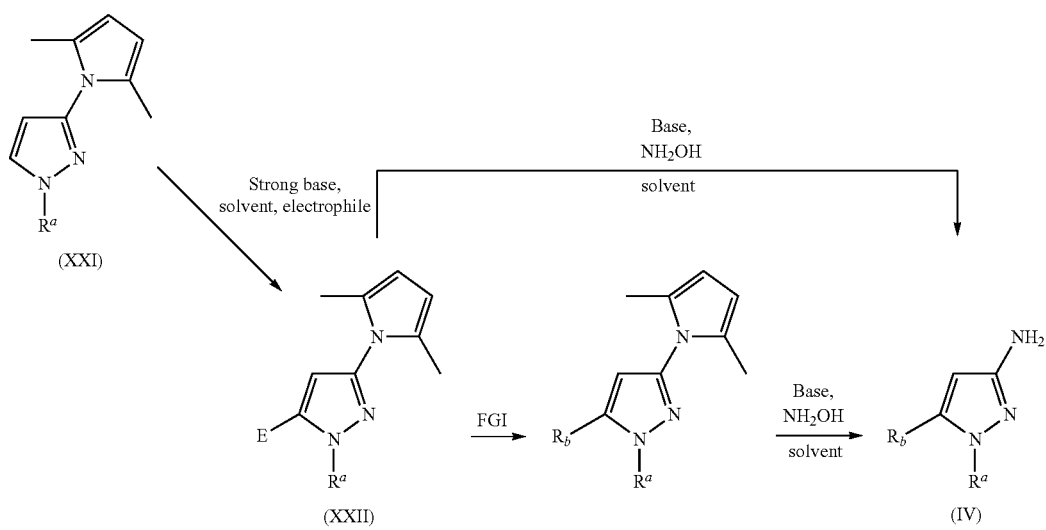

Phthalimide protected pyrazoles (XXIII) can be akylated with an appropriate base such as K₂CO₃, tBuOK, NaH, NaOH, in an appropriate solvent, such as THF and ether, with the appropriate alkyl halide, to afford (XXIV) and varying amounts of undesired (XXV). Removal of the protecting group, employing, propane-1,2-diamine affords the the desired amino pyrazoles (IV).

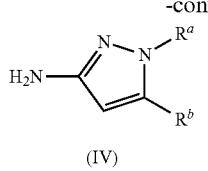

(IV)

Fused bycyclic amino pyrazoles of type (XXVI) can be prepared from Lactam intermediates (XXVII), wherein $R^{10}$ and $R^{11}$ are, for example, H or $C_1$-$C_6$ alkyl.

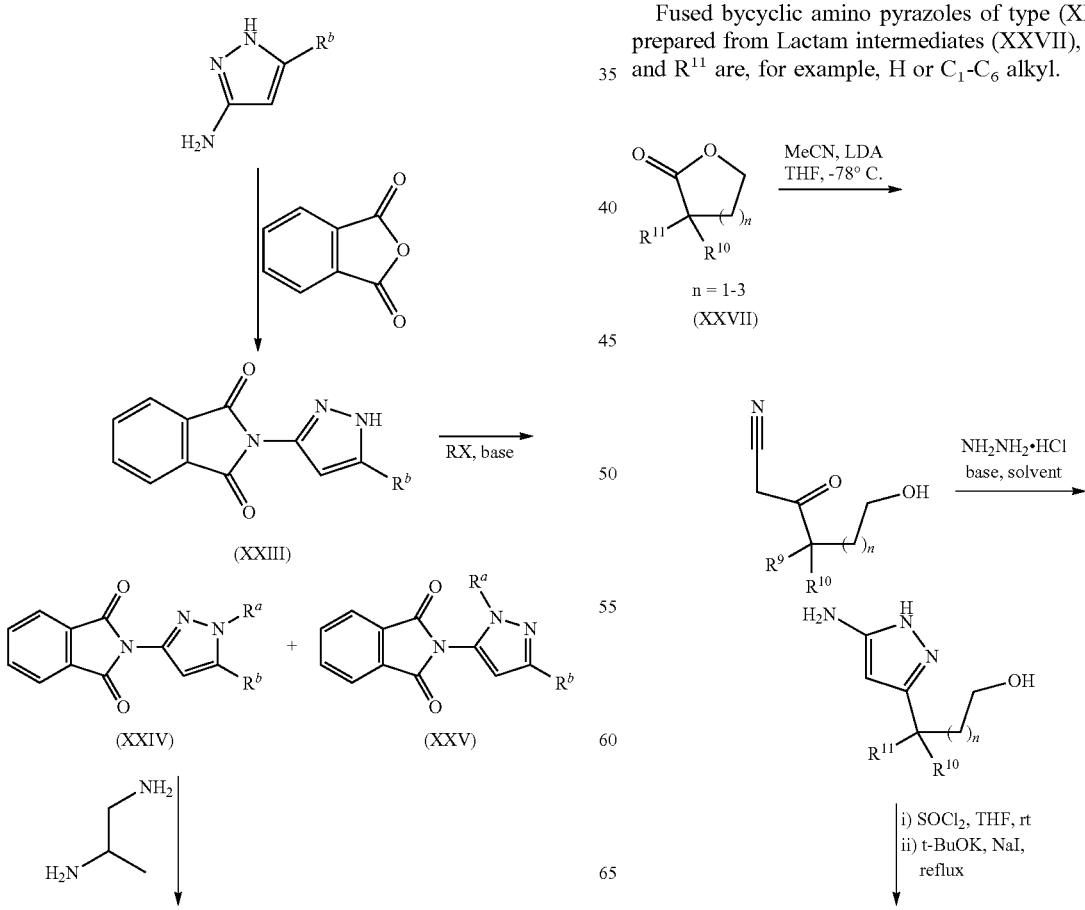

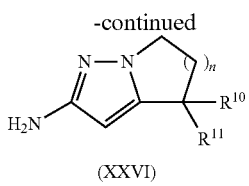

Fused bycyclic amino pyrazoles of type (XXVIII) can be prepared from cyclic ketone intermediates intermediates (XXIX).

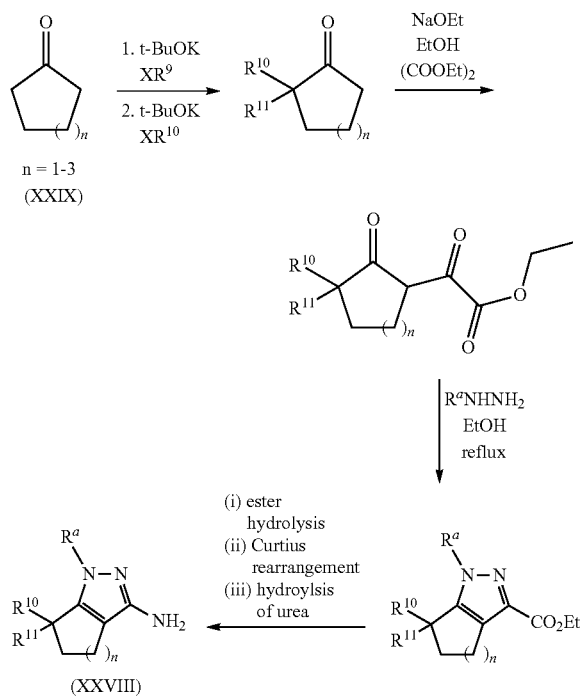

3-amino-4-nitrile substituted pyrazoles may be prepared as reported in the literature. Journal of Heterocyclic Chemistry 1982, vol. 19, p. 1267-1273.

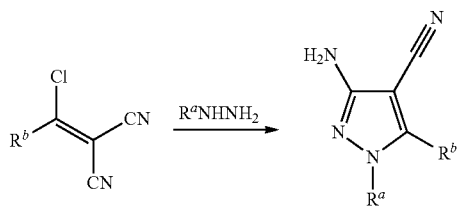

Suitable conditions for effecting these transformations are set out in texts such as J. March, Advanced Organic Chemistry, 4th ed. Wiley, New York, 1992.

The compounds of formula (I) according to the invention can be used as herbicides in unmodified form, as obtained in the synthesis, but they are generally formulated into herbicidal compositions in various ways using formulation adjuvants, such as carriers, solvents and surface-active substances. Therefore, the invention also relates to a herbicidal composition which comprises a herbicidally effective amount of a compound of formula (I) in addition to formulation adjuvants. The formulations can be in various physical forms, e.g. in the form of dusting powders, gels, wettable powders, water-dispersible granules, water-dispersible tablets, effervescent pellets, emulsifiable concentrates, micro-emulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO Specifications for Plant Protection Products, 5th Edition, 1999. Such formulations can either be used directly or they are diluted prior to use. The dilutions can be made, for example, with water, liquid fertilizers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof. The active ingredients can also be contained in very fine microcapsules consisting of a polymer. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art in this connection. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydro-furfuryl alcohol, hexanol, octanol, ethylene glycol, propylene glycol, glycerol, N-methyl-2-pyrrolidone and the like. Water is generally the carrier of choice for diluting the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecyl-benzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood N.J., 1981.

Further adjuvants that can usually be used in pesticidal formulations include crystallization inhibitors, viscosity modifiers, suspending agents, dyes, anti-oxidants, foaming agents, light absorbers, mixing auxiliaries, antifoams, complexing agents, neutralizing or pH-modifying substances and buffers, corrosion inhibitors, fragrances, wetting agents, take-up enhancers, micronutrients, plasticisers, glidants, lubricants, dispersants, thickeners, antifreezes, microbicides, and also liquid and solid fertilizers.

The compositions according to the invention can additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combination with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltriloxanes which are commercially available e.g. as Silwet L-77®, and also perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say, without oil additives.

Furthermore, the addition of an organic solvent to the oil additive/surfactant mixture may contribute to an additional enhancement of action. Suitable solvents are, for example, Solvesso® (ESSO) or Aromatic Solvent® (Exxon Corporation). The concentration of such solvents can be from 10 to 80% by weight of the total weight. Oil additives that are present in admixture with solvents are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkylpyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurogkem Pen-e-Trate®, to be added to the spray mixture as action-enhancing agent.

The herbicidal compositions generally comprise from 0.1 to 99% by weight, especially from 0.1 to 95% by weight, compounds of formula (I) and from 1 to 99.9% by weight of a formulation adjuvant which preferably includes from 0 to 25% by weight of a surface-active substance. Whereas commercial products will preferably be formulated as concentrates, the end user will normally employ dilute formulations.

The rates of application of compounds of formula (I) may vary within wide limits and depend on the nature of the soil, the method of application (pre- or post-emergence; seed dressing; application to the seed furrow; no tillage application etc.), the crop plant, the grass or weed to be controlled, the prevailing climatic conditions, and other factors governed by the method of application, the time of application and the target crop. The compounds of formula (I) according to the invention are generally applied at a rate of from 10 to 2000 g/ha, especially from 50 to 1000 g/ha.

Preferred formulations have especially the following compositions (%=percent by weight):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

Formulation Examples for Herbicides of Formula (I) (%=% by Weight)

| F1. Emulsifiable concentrates | a) | b) | c) | d) |
|---|---|---|---|---|
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for use in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient | 0.1% | 5% | 15% |
| highly dispersed silicic acid | 0.9% | 2% | 2% |
| inorganic carrier (diameter 0.1-1 mm) e.g. $CaCO_3$ or $SiO_2$ | 99.0% | 93% | 83% |

The active ingredient is dissolved in methylene chloride and applied to the carrier by spraying, and the solvent is then evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. $CaCO_3$ or $SiO_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

The invention also provides a method of controlling plants which comprises applying to the plants or to the locus thereof a herbicidally effective amount of a compound of formula (I).

The invention also provides a method of inhibiting plant growth which comprises applying to the plants or to the locus thereof a herbicidally effective amount of a compound of formula (I).

The invention also provides a method of controlling weeds in crops of useful plants, comprising applying to said weeds or to the locus of said weeds, or to said useful plants or to the locus of said useful plants, a compound or a composition of the invention.

The invention also provides a method of selectively controlling grasses and/or weeds in crops of useful plants which comprises applying to the useful plants or locus thereof or to the area of cultivation a herbicidally effective amount of a compound of formula (I).

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example: killing, retardation, leaf burn, albinism, dwarfing and the like. The term "plants" refers to all physical parts of a plant, including seeds, seedlings, saplings, roots, tubers, stems, stalks, foliage, and fruits. The term "locus" is intended to include soil, seeds, and seedlings, as well as established vegetation and includes not only areas where weeds may already be growing, but also areas where weeds have yet to emerge, and also to areas under cultivation with respect to crops of useful plants. "Areas under cultivation" include land on which the crop plants are already growing and land intended for cultivation with such crop plants. The term "weeds" as used herein means any undesired plant, and thus includes not only agronomically important weeds as described below, but also volunteer crop plants.

The compounds of the invention can be applied before or after planting of the crops, before weeds emerge (pre-emergence application) or after weeds emerge (post-emergence application), and are particularly effective when applied post-emergence to the weeds.

Crops of useful plants in which the composition according to the invention can be used include, but are not limited to, perennial crops, such as citrus fruit, grapevines, nuts, oil palms, olives, pome fruit, stone fruit and rubber, and annual arable crops, such as cereals, for example barley and wheat, cotton, oilseed rape, maize, rice, soy beans, sugar beet, sugar cane, sunflowers, ornamentals, switchgrass, turf and vegetables, especially cereals, maize and soy beans.

The grasses and weeds to be controlled may be both monocotyledonous species, for example *Agrostis, Alopecurus, Avena, Brachiaria, Bromus, Cenchrus, Cyperus, Digitaria, Echinochloa, Eriochloa, Lolium, Monochoria, Panicum, Poa, Rottboellia, Sagittaria, Scirpus, Setaria, Sida* and *Sorghum*, and dicotyledonous species, for example *Abutilon, Amaranthus, Chenopodium, Chrysanthemum, Euphorbia, Galium, Ipomoea, Kochia, Nasturtium, Polygonum, Sida, Sinapis, Solanum, Stellaria, Veronica, Viola* and *Xanthium*.

In all aspects of the invention, in a particular embodiment, the weeds, e.g. to be controlled and/or growth-inhibited may be monocotyledonous or dicotyledonous weeds, which are tolerant or resistant to one or more other herbicides for example, HPPD inhibitor herbicides such as mesotrione, PSII inhibitor herbicides such as atrazine or EPSPS inhibitors such as glyphosate. Such weeds include, but are not limited to resistant *Amaranthus* biotypes.

Crops are to be understood as also including those crops which have been rendered tolerant to herbicides or classes of herbicides (e.g. auxins or ALS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®, respectively.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesize such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

Any method of application to weeds/crop of useful plant, or locus thereof, which is routinely used in agriculture may be used, for example application by spray or broadcast method typically after suitable dilution of a compound of formula (I) (whether said compound is formulated and/or in combination with one or more further active ingredients and/or safeners, as described herein).

The compounds of formula (I) according to the invention can also be used in combination with other active ingredients, e.g. other herbicides, and/or insecticides, and/or acaricides, and/or nematocides, and/or molluscicides, and/or fungicides, and/or plant growth regulators. Such mixtures, and the use of such mixtures to control weeds and/or undesired plant growth, form yet further aspects of the invention. For the avoidance of doubt, mixtures of invention also include mixtures of two or more different compounds of formula (I). In particular, the present invention also relates to a composition of the invention which comprises at least one further herbicide in addition to the compound of formula (I).

When a compound of formula (I) is combined with at least one additional herbicide, the following mixtures of the compound of formula (I) are preferred. Compound of formula (I)+acetochlor, compound of formula (I)+acifluorfen, compound of formula (I)+acifluorfen-sodium, compound of formula (I)+aclonifen, compound of formula (I)+acrolein, compound of formula (I)+alachlor, compound of formula (I)+alloxydim, compound of formula (I)+allyl alcohol, compound of formula (I)+ametryn, compound of formula (I)+amicarbazone, compound of formula (I)+amidosulfuron, compound of formula (I)+aminocyclopyrachlor, compound of formula (I)+aminopyralid, compound of formula (I)+amitrole, compound of formula (I)+ammonium sulfamate, compound of formula (I)+anilofos, compound of formula (I)+asulam, compound of formula (I)+atrazine, formula (I)+aviglycine, formula (I)+azafenidin, compound of formula (I)+azimsulfuron, compound of formula (I)+BCPC, compound of formula (I)+beflubutamid, compound of formula (I)+benazolin, formula (I)+bencarbazone, compound of formula (I)+benfluralin, compound of formula (I)+benfuresate, compound of formula (I)+bensulfuron, compound of formula (I)+bensulfuron-methyl, compound of formula (I)+bensulide, compound of formula (I)+bentazone, compound of formula (I)+benzfendizone, compound of formula (I)+benzobicyclon, compound of formula (I)+benzofenap, compound of formula (I)+bicyclopyrone, compound of formula (I)+bifenox, compound of formula (I)+bilanafos, compound of formula (I)+bispyribac, compound of formula (I)+bispyribac-sodium, compound of formula (I)+borax, compound of formula (I)+bromacil, compound of formula (I)+bromobutide, formula (I)+bromophenoxim, compound of formula (I)+bromoxynil, compound of formula (I)+butachlor, compound of formula (I)+butafenacil, compound of formula (I)+butamifos, compound of formula (I)+butralin, compound of formula (I)+butroxydim, compound of formula (I)+butylate, compound of formula (I)+cacodylic acid, compound of formula (I)+calcium chlorate, compound of formula (I)+cafenstrole, compound of formula (I)+carbetamide, compound of formula (I)+carfentrazone, compound of formula (I)+carfentrazone-ethyl, compound of formula (I)+CDEA, compound of formula (I)+CEPC, compound of formula (I)+chlorflurenol, compound of formula (I)+chlorflurenol-methyl, compound of formula (I)+chloridazon, compound of formula (I)+chlorimuron, compound of formula (I)+chlorimuron-ethyl, compound of formula (I)+chloroacetic acid, compound of formula (I)+chlorotoluron, compound of formula (I)+chlorpropham, compound of formula (I)+chlorsulfuron, compound of formula (I)+chlorthal, compound of formula (I)+chlorthal-dimethyl, compound of formula (I)+cinidon-ethyl, compound of formula (I)+cinmethylin, compound of formula (I)+cinosulfuron, compound of formula (I)+cisanilide, compound of formula (I)+clethodim, compound of formula (I)+clodinafop, compound of formula (I)+clodinafop-propargyl, compound of formula (I)+clomazone, compound of formula (I)+clomeprop, compound of formula (I)+clopyralid, compound of formula (I)+cloransulam, compound of formula (I)+cloransulam-methyl, compound of formula (I)+CMA, compound of formula (I)+4-CPB, compound of formula (I)+CPMF, compound of formula (I)+4-CPP, compound of formula (I)+CPPC, compound of formula (I)+cresol, compound of formula (I)+cumyluron, compound of formula (I)+cyanamide, compound of formula (I)+cyanazine, compound of formula (I)+cycloate, compound of formula (I)+cyclosulfamuron, compound of formula (I)+cycloxydim, compound of formula (I)+cyhalofop, compound of formula (I)+cyhalofop-butyl, compound of formula (I)+2,4-D, compound of formula (I)+3,4-DA, compound of formula (I)+daimuron, compound of formula (I)+dalapon, compound of formula (I)+dazomet, compound of formula (I)+2,4-DB, compound of formula (I)+3,4-DB, compound of formula (I)+2,4-DEB, compound of formula (I)+desmedipham, formula (I)+desmetryn, compound of formula (I)+dicamba, compound of formula (I)+dichlobenil, compound of formula (I)+ortho-dichlorobenzene, compound of formula (I)+para-dichlorobenzene, compound of formula (I)+dichlorprop, compound of formula (I)+dichlorprop-P, compound of formula (I)+diclofop, compound of formula (I)+diclofop-methyl, compound of formula (I)+diclosulam, compound of formula (I)+difenzoquat, compound of formula (I)+difenzoquat metilsulfate, compound of formula (I)+diflufenican, compound of formula (I)+diflufenzopyr, compound of formula (I)+dimefuron, compound of formula (I)+dimepiperate, compound of formula (I)+dimethachlor, compound of formula (I)+dimethametryn, compound of formula (I)+dimethenamid, compound of formula (I)+dimethenamid-P, compound of formula (I)+dimethipin, compound of formula (I)+dimethylarsinic acid, compound of formula (I)+dinitramine, compound of formula (I)+dinoterb, compound of formula (I)+diphenamid, formula (I)+dipropetryn, compound of formula (I)+diquat, compound of formula (I)+diquat dibromide, compound of formula (I)+dithiopyr, compound of formula (I)+diuron, compound of formula (I)+DNOC, compound of formula (I)+3,4-DP, compound of formula (I)+DSMA, compound of formula (I)+EBEP, compound of formula (I)+endothal, compound of formula (I)+EPTC, compound of formula (I)+esprocarb, compound of formula (I)+ethalfluralin, compound of formula (I)+ethametsulfuron, compound of formula (I)+ethametsulfuron-methyl, formula (I)+ethephon, compound of formula (I)+ethofumesate, compound of formula (I)+ethoxyfen, compound of formula (I)+ethoxysulfuron, compound of formula (I)+etobenzanid, compound of formual (I)+fenoxaprop, compound of formula (I)+fenoxaprop-P, compound of formula (I)+fenoxaprop-ethyl, compound of formula (I)+fenoxaprop-P-ethyl, compound of formula (I)+fentrazamide, compound of formula (I)+ferrous sulfate, compound of formula (I)+flamprop-M, compound of formula (I)+flazasulfuron, compound of formula (I)+florasulam, compound of formula (I)+fluazifop, compound of formula (I)+fluazifop-butyl, compound of formula (I)+fluazifop-P, compound of formula (I)+fluazifop-P-butyl, formula (I)+fluazolate, compound of formula (I)+flucarbazone, compound of formula (I)+flucarbazone-sodium, compound of formula (I)+flucetosulfuron, compound of formula (I)+fluchloralin, compound of formula (I)+flufenacet, compound of formula (I)+flufenpyr, compound of formula (I)+flufenpyr-ethyl, formula (I)+flumetralin, compound of formula (I)+flumetsulam, compound of formula (I)+flumiclorac, compound of formula (I)+flumiclorac-pentyl, compound of formula (I)+flumioxazin, formula (I)+flumipropin, compound of formula (I)+fluometuron, compound of formula (I)+fluoroglycofen, compound of formula (I)+fluoroglycofen-ethyl, formula (I)+fluoxaprop, formula (I)+flupoxam, formula (I)+flupropacil, compound of formula (I)+flupropanate, compound of formula (I)+flupyrsulfuron, compound of formula (I)+flupyrsulfuron-methyl-sodium, compound of formula (I)+flurenol, compound of formula (I)+fluridone, compound of formula (I)+flurochloridone, compound of formula (I)+fluroxypyr, compound of formula (I)+flurtamone, compound of formula (I)+fluthiacet, compound of formula (I)+fluthiacet-methyl, compound of formula (I)+fomesafen, compound of formula (I)+foramsulfuron, compound of formula (I)+fosamine, compound of formula (I)+glufosinate, compound of formula (I)+glufosinate-ammonium, compound of formula (I)+glyphosate, compound of formula (I)+halauxifen, compound of formula (I)+halauxifen-methyl, compound of formula (I)+halosulfuron, compound of formula (I)+halosulfuron-methyl, compound of formula (I)+haloxyfop, compound of formula (I)+haloxyfop-P, compound of formula (I)+HC-252, compound of formula (I)+hexazinone, compound of formula (I)+imazamethabenz, compound of formula (I)+imazamethabenz-methyl, compound of formula (I)+imazamox, compound of formula (I)+imazapic, compound of formula (I)+imazapyr, compound of formula (I)+imazaquin, compound of formula (I)+imazethapyr, compound of formula (I)+imazosulfuron, compound of formula (I)+indanofan, compound of formula (I) and indaziflam, compound of formula (I)+iodomethane, compound of formula (I)+iodosulfuron, compound of formula (I)+iodosulfuron-methyl-sodium, compound of formula (I)+ioxynil, compound of formula (I) and ipfencarbazone, compound of formula (I)+isoproturon, compound of formula (I)+isouron, compound of formula (I)+isoxaben, compound of formula (I)+isoxachlortole, compound of formula (I)+isoxaflutole, formula (I)+isoxapyrifop, compound of formula (I)+karbutilate, compound of formula (I)+lactofen, compound of formula (I)+lenacil, compound of formula (I)+linuron, compound of formula (I)+MAA, compound of formula (I)+MAMA, compound of formula (I)+MCPA, compound of formula (I)+MCPA-thioethyl, compound of formula (I)+MCPB, compound of formula (I)+mecoprop, compound of formula (I)+mecoprop-P, compound of formula (I)+mefenacet, compound of formula (I)+mefluidide, compound of formula (I)+mesosulfuron, compound of formula (I)+mesosulfuron-methyl, compound of formula (I)+mesotrione, compound of formula (I)+metam, compound of formula (I)+metamifop, compound of formula (I)+metamitron, compound of formula (I)+metazachlor, compound of formula (I) and metazosulfuron, compound of formula (I)+methabenzthiazuron, formula (I)+methazole, a compound of formula (I) and methiozolin, compound of formula (I)+methylarsonic acid, compound of formula (I)+methyldymron, compound of formula (I)+methyl isothiocyanate, compound of formula (I)+metobenzuron, formula (I)+metobromuron, compound of formula (I)+metolachlor, compound of formula (I)+S-metolachlor, compound of formula (I)+metosulam, compound of formula (I)+metoxuron, compound of formula (I)+metribuzin, compound of formula (I)+metsulfuron, compound of formula (I)+metsulfuron-methyl, compound of formula (I)+MK-616, compound of formula (I)+molinate, compound of formula (I)+monolinuron, a compound of formula (I) and monosulfuron, a compound of formula (I) and monosulfuron-ester compound of formula (I)+MSMA, compound of formula (I)+naproanilide, compound of formula (I)+napropamide, compound of formula (I)+naptalam, formula (I)+NDA-402989, compound of formula (I)+neburon, compound of formula (I)+nicosulfuron, formula (I)+nipyraclofen, formula (I)+n-methyl glyphosate, compound of formula (I)+nonanoic acid, compound of formula (I)+norflurazon, compound of formula (I)+oleic acid (fatty acids), compound of formula (I)+orbencarb, compound of formula (I)+orthosulfamuron, compound of formula (I)+oryzalin, compound of formula (I)+oxadiargyl, compound of formula (I)+oxadiazon, compound of formula (I)+oxasulfuron, compound of formula (I)+oxaziclomefone, compound of formula (I)+oxyfluorfen, compound of formula (I)+paraquat, compound of formula (I)+paraquat dichloride, compound of formula (I)+pebulate, compound of formula (I)+pendimethalin, compound of formula (I)+penoxsulam, compound of formula (I)+pentachlorophenol, compound of formula (I)+pentanochlor, compound of formula (I)+pentoxazone, compound of formula (I)+pethoxamid, compound of formula (I)+petrolium oils, compound of formula (I)+phenmedipham, compound of formula (I)+phenmedipham-ethyl, compound of formula (I)+picloram, compound of formula (I)+picolinafen, compound of formula (I)+pinoxaden, compound of formula (I)+piperophos, compound of formula (I)+potassium arsenite, compound of formula (I)+potassium azide, compound of formula (I)+pretilachlor, compound of formula (I)+primisulfuron, compound of formula (I)+primisulfuron-methyl, compound of formula (I)+prodiamine, compound of formula (I)+profluazol, compound of formula (I)+profoxydim, formula (I)+prohexadione-calcium, compound of formula (I)+prometon, compound of formula (I)+prometryn, compound of formula (I)+propachlor, compound of formula (I)+propanil, compound of formula (I)+propaquizafop, compound of formula (I)+propazine, compound of formula (I)+propham, compound of formula (I)+propisochlor, compound of formula (I)+propoxycarbazone, compound of formula (I)+propoxycarbazone-sodium, compound of formula (I)+propyzamide, compound of formula (I)+prosulfocarb, compound of formula (I)+prosulfuron, compound of formula (I)+pyraclonil, compound of formula (I)+pyraflufen, compound of formula (I)+pyraflufen-ethyl, formula (I)+pyrasulfotole, compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyributicarb, compound of formula (I)+pyridafol, compound of formula (I)+pyridate, compound of formula (I)+pyriftalid, compound of formula (I)+pyriminobac, compound of formula (I)+pyriminobac-methyl, compound of formula (I)+pyrimisulfan, compound of formula (I)+pyrithiobac, compound of formula (I)+pyrithiobac-sodium, formula (I)+pyroxasulfone, formula (I)+pyroxulam, compound of formula (I)+quinclorac, compound of formula (I)+quinmerac, compound of formula (I)+quinoclamine, compound of formula (I)+quizalofop, compound of formula (I)+quizalofop-P, compound of formula (I)+quizalofop-ethyl, compound of formula (I)+quizalofop-P-ethyl, compound of formula (I)+rimsulfuron, compound of formula (I)+saflufenacil, compound of formula (I)+sethoxydim, compound of formula (I)+siduron, compound of formula (I)+simazine, compound of formula (I)+simetryn, compound of formula (I)+SMA, compound of formula (I)+sodium arsenite, compound of formula (I)+sodium azide, compound of formula (I)+sodium chlorate, compound of formula (I)+sulcotrione, compound of formula (I)+sulfentrazone, compound of formula (I)+sulfometuron, compound of formula (I)+sulfometuron-methyl, compound of formula (I)+sulfosate, compound of formula (I)+sulfosulfuron, compound of formula (I)+sulfuric acid, compound of formula (I)+tar oils, compound of formula (I)+2,3,6-TBA, compound of formula (I)+TCA, compound of formula (I)+TCA-sodium, formula (I)+tebutam, compound of formula (I)+tebuthiuron, formula (I)+tefuryltrione, compound of formula 1+tembotrione, compound of formula (I)+tepraloxydim, compound of formula (I)+terbacil, compound of formula (I)+terbumeton, compound of formula (I)+terbuthylazine, compound of formula (I)+terbutryn, compound of formula (I)+thenylchlor, compound of formula (I)+thiazafluron, compound of formula (I)+thiazopyr, compound of formula (I)+thifensulfuron, compound of formula (I)+thiencarbazone, compound of formula (I)+thifensulfuron-methyl, compound of formula (I)+thiobencarb, compound of formula (I)+tiocarbazil, compound of formula (I)+topramezone, compound of formula (I)+tralkoxydim, a compound of formula (I) and triafamone compound of formula (I)+tri-allate, compound of formula (I)+triasulfuron, compound of formula (I)+triaziflam, compound of formula (I)+tribenuron, compound of formula (I)+tribenuron-methyl, compound of formula (I)+tricamba, compound of formula (I)+triclopyr, compound of formula (I)+trietazine, compound of formula (I)+trifloxysulfuron, compound of formula (I)+trifloxysulfuron-sodium, compound of formula (I)+trifluralin, compound of formula (I)+triflusulfuron, compound of formula (I)+triflusulfuron-methyl, compound of formula (I)+trifop, compound of formula (I)+trifop-methyl, compound of formula (I)+trihydroxytriazine, compound of formula (I)+trinexapac-ethyl, compound of formula (I)+tritosulfuron, compound of formula (I)+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula (I)+2-[[8-chloro-3,4-dihydro-4-(4-methoxyphenyl)-3-oxo-2-quinoxalinyl]carbonyl-1,3-cyclohexanedione and the compound of formula (I)+VX-573.

In particular, the following mixtures are important:

mixtures of a compound of formula (I) with an acetanilide (e.g. compound of formula (I)+acetochlor, compound of formula (I)+dimethenamid, compound of formula (I)+metolachlor, compound of formula (I)+S-metolachlor, or compound of formula (I)+pretilachlor) or with other inhibitors of very long chain fatty acid esterases (VLCFAE) (e.g. compound of formula (I)+pyroxasulfone);

mixtures of a compound of formula (I) with an HPPD inhibitor (e.g. compound of formula (I)+isoxaflutole, compound of formula (I)+mesotrione, compound of formula (I)+pyrasulfotole, compound of formula (I)+sulcotrione, compound of formula (I)+tembotrione, compound of formula (I)+topramezone, compound of formula (I)+bicyclopyrone;

mixtures of a compound of formula (I) with a triazine (e.g. compound of formula (I)+atrazine, or compound of formula (I)+terbuthylazine);

mixtures of a compound of formula (I) with glyphosate;

mixtures of a compound of formula (I) with glufosinate-ammonium;

mixtures of a compound of formula (I) with a PPO inhibitor (e.g. compound of formula (I)+acifluorfen-sodium, compound of formula (I)+butafenacil, compound of formula (I)+carfentrazone-ethyl, compound of formula (I)+cinidon-ethyl, compound of formula (I)+flumioxazin, compound of formula (I)+fomesafen, compound of formula (I)+lactofen, or compound of formula (I)+SYN 523 ([3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester) (CAS RN 353292-31-6)).

Whilst two-way mixtures of a compound of formula (I) and another herbicide are explicitly disclosed above, the skilled man will appreciate that the invention extends to three-way, and further multiple combinations comprising the above two-way mixtures. In particular, the invention extends to:

mixtures of a compound of formula (I) with a triazine and an HPPD inhibitor (e.g. compound of formula (I)+triazine+isoxaflutole, compound of formula (I)+triazine+mesotrione, compound of formula (I)+triazine+pyrasulfotole, compound of formula (I)+triazine+sulcotrione, compound of formula (I)+triazine+tembotrione, compound of formula (I)+triazine+topramezone, compound of formula (I)+triazine+bicyclopyrone;

mixtures of a compound of formula (I) with glyphosate and an HPPD inhibitor (e.g. compound of formula (I)+glyphosate+isoxaflutole, compound of formula (I)+glyphosate+mesotrione, compound of formula (I)+glyphosate+pyrasulfotole, compound of formula (I)+glyphosate+sulcotrione, compound of formula (I)+glyphosate+tembotrione, compound of formula (I)+glyphosate+topramezone, compound of formula (I)+glyphosate+bicyclopyrone;

mixtures of a compound of formula (I) with glufosinate-ammonium and an HPPD inhibitor (e.g. compound of formula (I)+glufosinate-ammonium+isoxaflutole, compound of formula (I)+glufosinate-ammonium+mesotrione, compound of formula (I)+glufosinate-ammonium+pyrasulfotole, compound of formula (I)+glufosinate-ammonium+sulcotrione, compound of formula (I)+glufosinate-ammonium+tembotrione, compound of formula (I)+glufosinate-ammonium+topramezone, compound of formula (I)+glufosinate-ammonium+bicyclopyrone;

mixtures of a compound of formula (I) with a VLCFAE inhibitor and an HPPD inhibitor (e.g. compound of formula (I)+S-metolachlor+isoxaflutole, compound of formula (I)+S-metolachlor+mesotrione, compound of formula (I)+S-metolachlor+pyrasulfotole, compound of formula (I)+S-metolachlor+sulcotrione, compound of formula (I)+S-metolachlor+tembotrione, compound of formula (I)+S-metolachlor+topramezone, compound of formula (I)+S-metolachlor+bicyclopyrone, compound of formula (I)+acetochlor+isoxaflutole, compound of formula (I)+acetochlor+mesotrione, compound of formula (I)+acetochlor+pyrasulfotole, compound of formula (I)+acetochlor+sulcotrione, compound of formula (I)+acetochlor+tembotrione, compound of formula (I)+acetochlor+topramezone, compound of formula (I)+acetochlor+bicyclopyrone, compound of formula (I)+pyroxasulfone+isoxaflutole, compound of formula (I)+pyroxasulfone+mesotrione, compound of formula (I)+pyroxasulfone+pyrasulfotole, compound of formula (I)+pyroxasulfone+sulcotrione, compound of formula (I)+pyroxasulfone+tembotrione, compound of formula (I)+pyroxasulfone+topramezone, compound of formula (I)+pyroxasulfone+bicyclopyrone, compound of formula (I)+S-metolachlor+mesotrione+bicyclopyrone;

mixtures of a compound of formula (I) with glyphosate and a VLCFAE inhibitor (e.g. compound of formula (I)+glyphosate+S-metolachlor, compound of formula (I)+glyphosate+acetochlor, compound of formula (I)+glyphosate+pyroxasulfone).

Particularly preferred are mixtures of the compound of formula (I) with mesotrione, bicyclopyrone, isoxaflutole, tembotrione, topramezone, sulcotrione, pyrasulfotole, metolachlor, S-metolachlor, acetochlor, pyroxasulfone, P-dimethenamid, dimethenamid, flufenacet, pethoxamid, atrazine, terbuthylazine, bromoxynil, metribuzin, amicarbazone, bentazone, ametryn, hexazinone, diuron, tebuthiuron, glyphosate, paraquat, diquat, glufosinate, acifluorfen-sodium, butafenacil, carfentrazone-ethyl, cinidon-ethyl, flumioxazin, fomesafen, lactofen, [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester.

The mixing partners of the compound of formula (I) may also be in the form of esters or salts, as mentioned e.g. in The Pesticide Manual, 14th Edition (BCPC), 2006. The reference to acifluorfen-sodium also applies to acifluorfen, the reference to dimethenamid also applies to dimethenamid-P, the reference to glufosinate-ammonium also applies to glufosinate, the reference to bensulfuron-methyl also applies to bensulfuron, the reference to cloransulam-methyl also applies to cloransulam, the reference to flamprop-M also applies to flamprop, and the reference to pyrithiobac-sodium also applies to pyrithiobac, etc.

The mixing ratio of the compound of formula (I) to the mixing partner is preferably from 1:100 to 1000:1.

The mixtures can advantageously be used in the above-mentioned formulations (in which case "active ingredient" relates to the respective mixture of compound of formula (I) with the mixing partner).

The compounds of formula (I) according to the invention can also be used in combination with one or more safeners. Likewise, mixtures of a compound of formula (I) according to the invention with one or more further active ingredients, in particular with one or more further herbicides, can also be used in combination with one or more safeners. The term "safener" as used herein means a chemical that when used in combination with a herbicide reduces the undesirable effects of the herbicide on non-target organisms, for example, a safener protects crops from injury by herbicides but does not prevent the herbicide from killing the weeds. Where a compound of formula (I) is combined with a safener, the following combinations of the compound of formula (I) and the safener are particularly preferred. Compound of formula (I)+AD 67 (MON 4660), compound of formula (I)+benoxacor, compound of formula (I)+cloquintocet-mexyl, compound of formula (I)+cyometrinil and a compound of formula (I)+the corresponding (Z) isomer of cyometrinil, compound of formula (I)+cyprosulfamide (CAS RN 221667-31-8), compound of formula (I)+dichlormid, compound of formula (I) and dicyclonon, compound of formula (I) and dietholate, compound of formula (I)+fenchlorazole-ethyl, compound of formula (I)+fenclorim, compound of formula (I)+flurazole, compound of formula (I)+fluxofenim, compound of formula (I)+furilazole and a compound of formula (I)+the corresponding R isomer or furilazome, compound of formula (I)+isoxadifen-ethyl, compound of formula (I)+mefenpyr-diethyl, compound of formula (I) and mephenate, compound of formula (I)+oxabetrinil, compound of formula (I)+naphthalic anhydride (CAS RN 81-84-5), compound of formula (I) and TI-35, compound of formula (I)+N-isopropyl-4-(2-methoxy-benzoylsulfamoyl)-benzamide (CAS RN 221668-34-4) and a compound of formula (I)+N-(2-methoxybenzoyl)-4-[(methylaminocarbonyl)amino]benzenesulfonamide. Particularly preferred are mixtures of a compound of formula (I) with benoxacor, a compound of formula (I) with cloquintocet-mexyl, a compound of formula (I)+cyprosulfamide and a compound of formula (I) with N-(2-methoxybenzoyl)-4-[(methylaminocarbonyl)amino]benzenesulfonamide.

The safeners of the compound of formula (I) may also be in the form of esters or salts, as mentioned e.g. in The Pesticide Manual, 14th Edition (BCPC), 2006. The reference to cloquintocet-mexyl also applies to cloquintocet and to a lithium, sodium, potassium, calcium, magnesium, aluminium, iron, ammonium, quaternary ammonium, sulfonium or phosphonium salt thereof as disclosed in WO02/34048 and the reference to fenchlorazole-ethyl also applies to fenchlorazole, etc.

Preferably the mixing ratio of compound of formula (I) to safener is from 100:1 to 1:10, especially from 20:1 to 1:1.

The mixtures can advantageously be used in the above-mentioned formulations (in which case "active ingredient" relates to the respective mixture of compound of formula (I) and any further active ingredient, in particular a further herbicide, with the safener).

It is possible that the safener and a compound of formula (I) and one or more additional herbicide(s), if any, are applied simultaneously. For example, the safener, a compound of formula (I) and one or more additional herbicide(s), if any, might be applied to the locus pre-emergence or might be applied to the crop post-emergence. It is also possible that the safener and a compound of formula (I) and one or more additional herbicide(s), if any, are applied sequentially. For example, the safener might be applied before sowing the seeds as a seed treatment and a compound of formula (I) and one or more additional herbicides, if any, might be applied to the locus pre-emergence or might be applied to the crop post-emergence.

Preferred mixtures of a compound of formula (I) with further herbicides and safeners include:

Mixtures of a compound of formula (I) with S-metolachlor and a safener, particularly benoxacor.

Mixtures of a compound of formula (I) with isoxaflutole and a safener.

Mixtures of a compound of formula (I) with mesotrione and a safener.

Mixtures of a compound of formula (I) with sulcotrione and a safener.

Mixtures of a compound of formula (I) with tembotrione and a safener.

Mixtures of a compound of formula (I) with topramezone and a safener.

Mixtures of a compound of formula (I) with bicyclopyrone and a safener.

Mixtures of a compound of formula (I) with a triazine and a safener.

Mixtures of a compound of formula (I) with a triazine and isoxaflutole and a safener.

Mixtures of a compound of formula (I) with a triazine and mesotrione and a safener.

Mixtures of a compound of formula (I) with a triazine and sulcotrione and a safener.

Mixtures of a compound of formula (I) with a triazine and tembotrione and a safener.

Mixtures of a compound of formula (I) with a triazine and topramezone and a safener.

Mixtures of a compound of formula (I) with a triazine and bicyclopyrone and a safener.

Mixtures of a compound of formula (I) with glyphosate and a safener.

Mixtures of a compound of formula (I) with glyphosate and isoxaflutole and a safener.

Mixtures of a compound of formula (I) with glyphosate and mesotrione and a safener.

Mixtures of a compound of formula (I) with glyphosate and sulcotrione and a safener.

Mixtures of a compound of formula (I) with glyphosate and tembotrione and a safener.

Mixtures of a compound of formula (I) with glyphosate and topramezone and a safener.

Mixtures of a compound of formula (I) with glyphosate and bicyclopyrone and a safener.

Mixtures of a compound of formula (I) with glufosinate-ammonium and a safener.

Mixtures of a compound of formula (I) with glufosinate-ammonium and isoxaflutole and a safener.

Mixtures of a compound of formula (I) with glufosinate-ammonium and mesotrione and a safener.

Mixtures of a compound of formula (I) with glufosinate-ammonium and sulcotrione and a safener.

Mixtures of a compound of formula (I) with glufosinate-ammonium and tembotrione and a safener.

Mixtures of a compound of formula (I) with glufosinate-ammonium and topramezone and a safener.

Mixtures of a compound of formula (I) with glufosinate-ammonium and bicyclopyrone and a safener.

Mixtures of a compound of formula (I) with S-metolachlor and a safener.

Mixtures of a compound of formula (I) with S-metolachlor and isoxaflutole and a safener.

Mixtures of a compound of formula (I) with S-metolachlor and mesotrione and a safener.

Mixtures of a compound of formula (I) with S-metolachlor and sulcotrione and a safener.

Mixtures of a compound of formula (I) with S-metolachlor and tembotrione and a safener.

Mixtures of a compound of formula (I) with S-metolachlor and topramezone and a safener.

Mixtures of a compound of formula (I) with S-metolachlor and bicyclopyrone and a safener.

Mixtures of a compound of formula (I) with pyroxasulfone and a safener.

Mixtures of a compound of formula (I) with pyroxasulfone and isoxaflutole and a safener.

Mixtures of a compound of formula (I) with pyroxasulfone and mesotrione and a safener.

Mixtures of a compound of formula (I) with pyroxasulfone and sulcotrione and a safener.

Mixtures of a compound of formula (I) with pyroxasulfone and tembotrione and a safener.

Mixtures of a compound of formula (I) with pyroxasulfone and topramezone and a safener.

Mixtures of a compound of formula (I) with pyroxasulfone and bicyclopyrone and a safener.

Mixtures of a compound of formula (I) with acetochlor and a safener.

Mixtures of a compound of formula (I) with acetochlor and isoxaflutole and a safener.

Mixtures of a compound of formula (I) with acetochlor and mesotrione and a safener.

Mixtures of a compound of formula (I) with acetochlor and sulcotrione and a safener.

Mixtures of a compound of formula (I) with acetochlor and tembotrione and a safener.

Mixtures of a compound of formula (I) with acetochlor and topramezone and a safener.

Mixtures of a compound of formula (I) with acetochlor and bicyclopyrone and a safener.

Mixtures of a compound of formula (I) with S-metolachlor and mesotrione and bicyclopyrone and a safener.

Mixtures of a compound of formula (I) with S-metolachlor and a triazine and mesotrione and bicyclopyrone and a safener.

Various aspects and embodiments of the present invention will now be illustrated in more detail by way of example. It will be appreciated that modification of detail may be made without departing from the scope of the invention.

For the avoidance of doubt, where a literary reference, patent application, or patent, is cited within the text of this application, the entire text of said citation is herein incorporated by reference.

EXAMPLES

Preparation Examples

The following abbreviations were used in this section: s=singlet; bs=broad singlet; d=doublet; dd=double doublet; dt=double triplet; t=triplet, tt=triple triplet, q=quartet, sept=septet; m=multiplet; RT=retention time, MH$^+$=molecular mass of the molecular cation.

1H NMR spectra were recorded at 400 MHz either on a Varian Unity Inova instrument or Bruker AVANCE-II instrument.

Where $R^2$ is not H, the compounds may exist in a mixture of diastereoisomers, which may be observed by LC-MS and NMR. The stereochemistry of the chiral centre at the carbon containing the $R^3$ group was generally found to interconvert in solution at room temperature. Depending on the nature of $R_2$ substitution and the conditions for product synthesis, purification and analysis the ratio of diastereromers may change.

Example 1—Preparation of 4-hydroxy-1,5-dimethyl-3-[1-methyl-5-(trifluoromethyl)pyrazol-3-yl]imidazolidin-2-one (A2)

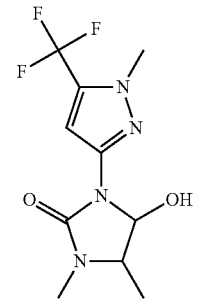 [SMILES: CC1C(O)N(c2cc(C(F)(F)F)n(C)n2)C(=O)N1C]

Procedure for Synthesis of 1,1-dimethoxy-N-methyl-propan-2-amine (Step 1)

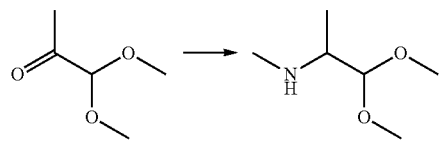

Ti(O-iPr)$_4$ (34.3 g, 2 equiv.) was cooled to 10° C. under a nitrogen atmosphere then ethanol (89 mL) was added followed by 1,1-dimethoxypropan-2-one (7.14 g, 1 equiv), methylamine hydrochloride (8.16 g, 2 equiv.) and triethylamine (16.8 mL, 2 equiv.). The reaction was stirred at room temperature for 15 h. The reaction was cooled to 10° C. and then NaBH$_4$ (3.43 g, 1.5 equiv.) was added and the reaction was stirred at room temperature for 6 h. The reaction was cooled to 10° C., then carefully over 10 minutes poured into ice cold aqueous ammonia (180 mL, 2M). The mixture was filtered, washing through with DCM (300 mL). The layers were separated and then the aqueous layer was extracted with further DCM (3×100 mL). The combined DCM layers were dried (Na$_2$SO$_4$), filtered and evaporated with care as to not lose any of the volatile product. This crude material was distilled on a Kugelrohr (70 to 110° C. 14 mBar) to give product (4.41 g) as a colourless oil, which was used without further purification.

$^1$H NMR (400 MHz, CDCl$_3$) δ 4.11 (d, 1H), 3.41 (s, 6H), 2.69 (pentet, 1H), 2.43 (s, 3H), 1.06 (d, 3H).

Procedure for Synthesis of phenyl N-[1-methyl-5-(trifluoromethyl)pyrazol-3-yl]carbamate (Step 2)

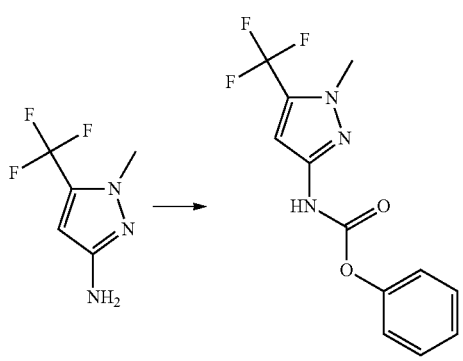 [SMILES: Cn1nc(N)cc1C(F)(F)F ; Cn1nc(NC(=O)Oc2ccccc2)cc1C(F)(F)F]

1-methyl-5-(trifluoromethyl)pyrazol-3-amine (commercially available, 30 g, 181.69 mmol) was dissolved in THF (500 mL) and pyridine (29.5 mL) was added. The solution was then cooled with an ice water bath and phenyl carbonochloridate (27.35 mL, 218.03 mmol) added dropwise, taking care to keep the internal reaction temperature below 5° C. The reaction was stirred for 1.5 h under ice-bath cooling and then the reaction was allowed to warm to room temperature and stirred for 1 h. Water (300 mL) was carefully added to the reaction with stirring. Ethyl acetate (500 mL) was added and the layers separated. The organics were washed with water (250 mL×3), brine (150 mL) and dried (MgSO$_4$). The solvent was then removed in vacuo to give a residue, which was dissolved in toluene (60 mL) and evaporated to dryness and this process was repeated. This provided a crude product, which was used without further purification.

LC-MS: (positive ES MH+ 286).

Procedure for Synthesis of 1-(2,2-dimethoxy-1-methyl-ethyl)-1-methyl-3-[1-methyl-5-(trifluoromethyl)pyrazol-3-yl]urea (Step 3)

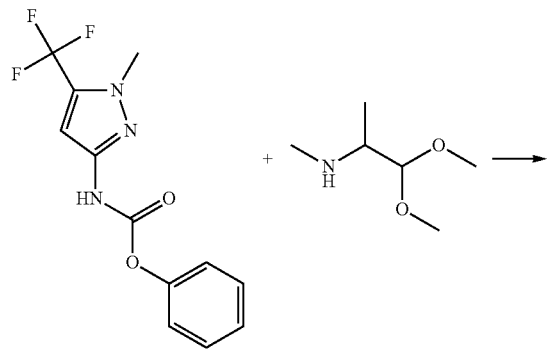

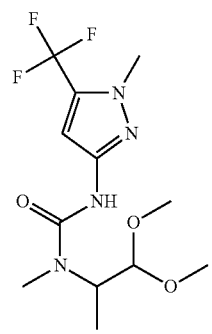

Phenyl N-[1-methyl-5-(trifluoromethyl)pyrazol-3-yl]carbamate (6 g, 21.04 mmol) was suspended in 1,4-dioxane (21 mL) under a nitrogen atmosphere and 1,1-dimethoxy-N-methyl-propan-2-amine (3.08 g, 23.140 mmol) and N-ethyl-N-isopropyl-propan-2-amine (11.0 mL, 63.11 mmol) were added. The reaction was stirred at room temperature for 2 days. The reaction was then diluted with NaHCO$_3$ (30 mL) and extracted with EtOAc (3×30 mL). The organics were washed with brine, dried over magnesium sulfate and the solvent removed in vacuo, then the residue was chromatographed on silica eluting with ethyl acetate in DCM. Fractions containing product were evaporated to give the desired product (6.03 g, 88%).

LC-MS: (positive ES MH+ 325).

Procedure for Synthesis of 4-hydroxy-1,5-dimethyl-3-[1-methyl-5-(trifluoromethyl)pyrazol-3-yl]imidazolidin-2-one (A2) (Step 4)

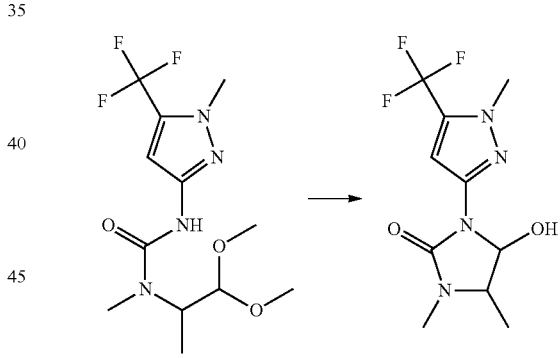

1-(2,2-dimethoxy-1-methyl-ethyl)-1-methyl-3-[1-methyl-5-(trifluoromethyl)pyrazol-3-yl]urea (4.685 g, 14.45 mmol) was dissolved in water (14.45 mL) and acetic acid (14.45 mL). The reaction was separated into two vials and each heated in the microwave for 25 minutes. The reactions were recombined and diluted with water (50 mL) and then extracted with ethyl acetate (3×50 mL). The organics were combined, dried over magnesium sulfate and evaporated in vacuo. the residue was chromatographed on silica eluting with ethyl acetate in DCM. Fractions containing product were evaporated to give the desired product (2.83 g, 70%).

Major diastereomer: $^1$H NMR (400 MHz, CDCl$_3$) δ 6.99 (s, 1H), 5.39 (d, 1H), 4.24 (br s, 1H), 3.86 (s, 3H), 3.50 (m, 1H), 2.88 (s, 3H), 1.30 (d, 3H).

Minor diastereomer: $^1$H NMR (400 MHz, CDCl$_3$) δ 6.99 (s, 1H), 5.71 (d, 1H), 4.01 (br s, 1H), 3.86 (s, 3H), 3.70 (m, 1H), 2.83 (s, 3H), 1.36 (d, 3H).

LC-MS: (positive ES MH+ 281).

Example 2—Preparation of 4-hydroxy-1-methoxy-5-methyl-3-[1-methyl-5-(trifluoromethyl)pyrazol-3-yl]imidazolidin-2-one (A4)

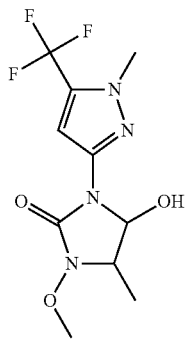 [SMILES: CON1C(=O)N(c2cc(C(F)(F)F)n(C)n2)C(O)C1C]

Procedure for Synthesis of N,1,1-trimethoxypropan-2-imine (Step-1)

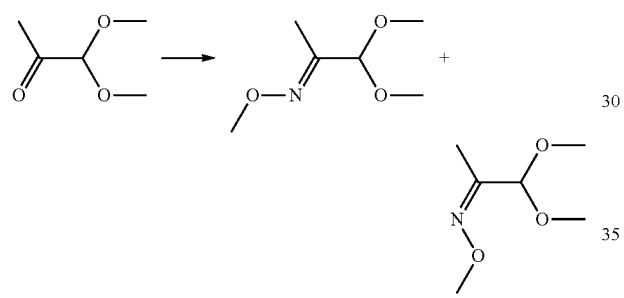

Methoxylamine hydrochloride (21.2 g) was suspended in methanol (65 mL) then potassium acetate (50.4 g, quickly ground in pestle and mortar to break up lumps) was added all at once and the thick white suspension resulting was stirred at room temp for 15 mins then cooled to 15° C. and then 1,1-dimethoxypropan-2-one (30 g) was added slowly over 25 mins. The reaction was stirred at room temperature for 50 mins and then diluted with DCM (200 mL), then sat. NaHCO$_3$ (aq) (100 mL) was added cautiously over 15 mins. After effervescence subsided, the layers were separated, extracted with further DCM (2×80 mL), dried Na$_2$SO$_4$, filtered and concentrated at 220 mbar and 35° C. (care as desired product is volatile) to give product (37 g) as an amber liquid, which was used without further purification.

$^1$H NMR (CDCl$_3$) showed a 3:1 ratio of E:Z isomers

Procedure for Synthesis of N,1,1-trimethoxypropan-2-amine (Step-2)

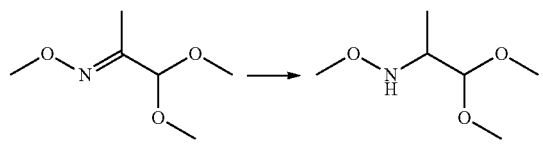

N,1,1-trimethoxypropan-2-imine (20 g) was dissolved in acetic acid (80 mL) then was cooled to 13° C. NaBH$_3$CN (9.82 g) was added portionwise over 10 mins. After 18 hrs at room temperature, the reaction was concentrated to remove bulk of HOAc then residue dissolved in DCM (300 mL) and satd. NaHCO$_3$ (aq) (300 mL) was added slowly with stirring. The mixture was stirred at rt for 90 mins, and then 40% NaOH (aq) was added until the solution reached pH 12. The layers were separated, extracted with further DCM (3×100 mL). The combined DCM layers were dried (Na$_2$SO$_4$), filtered and evaporated to give 16.4 g of crude product as a pale amber oil, which was further purified by Kugelrohr distillation (120° C. at 70 mBar) to give product (12.0 g, 59% yield) which was approximately 95% pure by NMR and used without further purification.

Procedure for Synthesis of 1-(2,2-dimethoxy-1-methyl-ethyl)-1-methoxy-3-[1-methyl-5-(trifluoromethyl)pyrazol-3-yl]urea (Step-3)

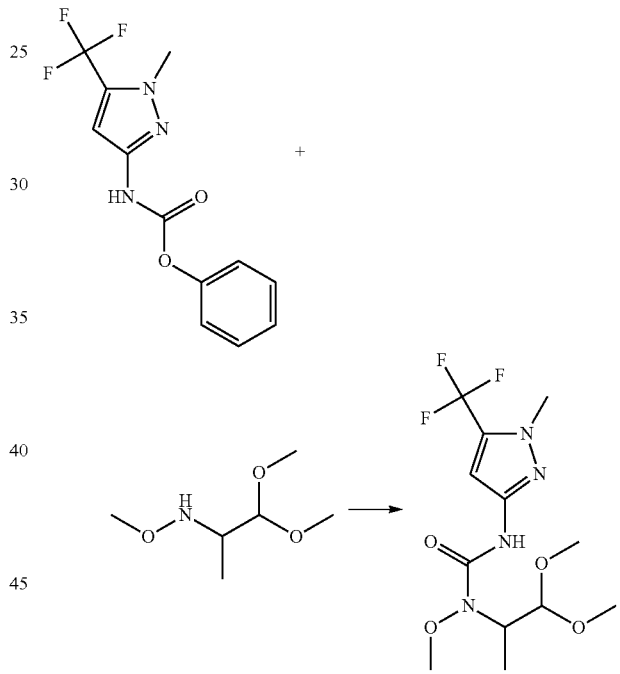

Phenyl N-[1-methyl-5-(trifluoromethyl)pyrazol-3-yl]carbamate (3.5 g, 12 mmol) was suspended in 1,4-dioxane (10 mL) under a nitrogen atmosphere and N,1,1-trimethoxypropan-2-amine (0.95 equiv., 12 mmol) was added. The reaction was then heated to 100° C. using a heating block with stirring. N-ethyl-N-isopropyl-propan-2-amine (3 equiv., 37 mmol) was added and the reaction was heated at 100° C. for 2 h and 10 mins before the reaction was cooled to room temperature and 2N HCl added until the reaction was acidic (pH 1-2, 28 mL). The reaction was extracted with EtOAc (2×30 mL), dried over magnesium sulfate and the solvent removed in vacuo. The residue was chromatographed on silica eluting with ethyl acetate in Hexane. Fractions containing product were evaporated to give the desired crude product, which was used as in the next step without further purification.

LC-MS: (positive ES MH+ 286).

Procedure for Synthesis of 4-hydroxy-1-methoxy-5-methyl-3-[1-methyl-5-(trifluoromethyl)pyrazol-3-yl]imidazolidin-2-one (A4) (Step-4)

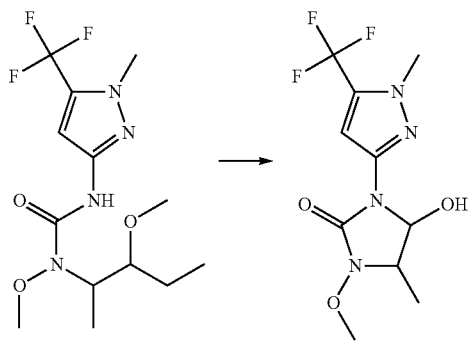 [SMILES: CCC(OC)C(C)N(OC)C(=O)Nc1cc(C(F)(F)F)n(C)n1 ; CON1C(=O)N(c2cc(C(F)(F)F)n(C)n2)C(O)C1C]

1-(2,2-dimethoxy-1-methyl-ethyl)-1-methoxy-3-[1-methyl-5-(trifluoromethyl)pyrazol-3-yl]urea (1.393 g, 4.093 mmol) was dissolved in acetone (16.37 mL) and water (0.2456 mL) and Amberlyst 15 resin (0.164 g, 40 g/mol) was added. The reaction was heated to 60° C. and shaken on an orbital shaker for 2 h. The amberlyst was removed by filtration and the solvent reduced in vacuo. The residue was chromatographed on silica eluting with ethyl acetate in Hexane. Fractions containing product were evaporated to give the desired product (1.19 g, 98%).

Major diastereomer: 1H NMR (400 MHz, CDCl$_3$) δ 7.01 (s, 1H), 5.29 (m, 1H), 4.35 (m, 1H), 3.82 (m, 6H), 3.65 (m, 1H), 1.43 (d, 3H,).

Minor diastereomer): 7.00 (s, 1H), 5.61 (m, 1H), 3.95 (m, 1H), 3.82 (m, 6H), 3.73 (m, 1H), 1.46 (d, 3H).

LC-MS: (positive ES MH+ 295).

Example 3—Preparation of 5-ethoxy-4-hydroxy-1-methyl-3-[1-methyl-5-(trifluoromethyl)pyrazol-3-yl]imidazolidin-2-one (A8) and 4,5-dihydroxy-1-methyl-3-[1-methyl-5-(trifluoromethyl)pyrazol-3-yl]imidazolidin-2-one (A12)

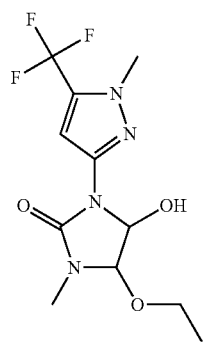 [SMILES: CCOC1C(O)N(c2cc(C(F)(F)F)n(C)n2)C(=O)N1C]

Procedure for Synthesis of 1-methyl-3-[1-methyl-5-(trifluoromethyl)pyrazol-3-yl]urea (Step-1)

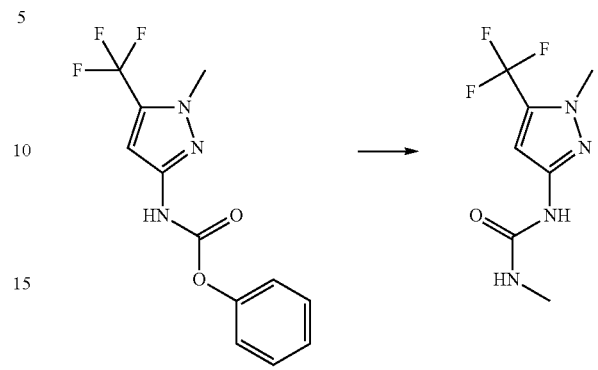

Phenyl N-[1-methyl-5-(trifluoromethyl)pyrazol-3-yl]carbamate (6 g, 21.04 mmol) was suspended in 1,4-dioxane (21 mL) under a nitrogen atmosphere and then methylamine in THF (2M, 11 mL) and N-ethyl-N-isopropyl-propan-2-amine (11.0 mL, 63.109 mmol) were added. The reaction was stirred at room temperature overnight. The precipitate was separated by filtration and the eluant diluted with NaHCO$_3$ (30 mL) and extracted with EtOAc (3×30 mL). The organics were washed with brine, dried over magnesium sulfate and the solvent was removed in vacuo. The residue was chromatographed on silica eluting with ethyl acetate in DCM. Fractions containing product were evaporated to give the desired product (3.76 g, 80%).

Procedure for Synthesis of 5-ethoxy-4-hydroxy-1-methyl-3-[1-methyl-5-(trifluoromethyl)pyrazol-3-yl]imidazolidin-2-one (A8) and 4,5-dihydroxy-1-methyl-3-[1-methyl-5-(trifluoromethyl)pyrazol-3-yl]imidazolidin-2-one (A12) (Step-2)

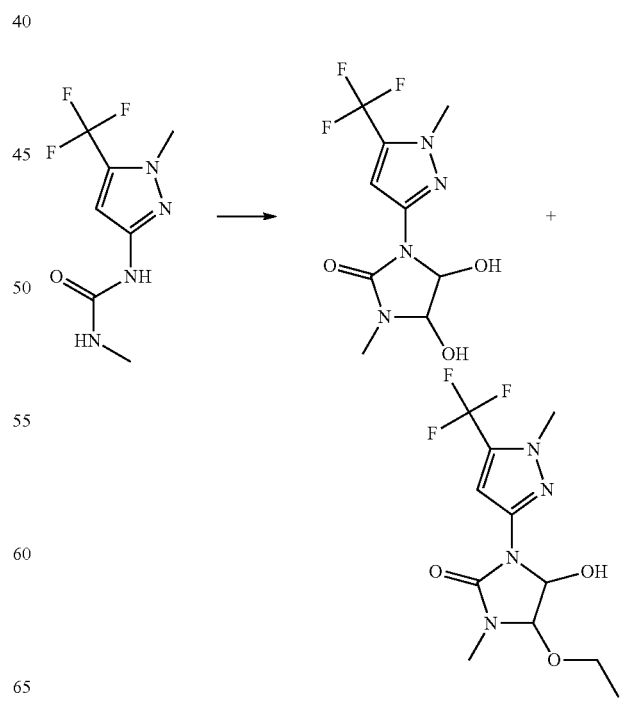

1-methyl-3-[1-methyl-5-(trifluoromethyl)pyrazol-3-yl]urea (3 g, 13.503 mmol) was dissolved in ethanol (135.03 mL) and glyoxal (40% aqueous solution) (81.019 mmol, 9.293 mL) and 4-methylbenzenesulfonic acid (0.116 g 0.68 mmol) were added. The mixture was then stirred at reflux for 3 h, before the reaction was cooled and the solvent removed in vacuo. The residue was dissolved in ethyl acetate (80 mL) and washed with NaHCO$_3$ (50 mL) then brine (30 mL). The organics were dried over magnesium sulfate and the solvent removed in vacuo. The residue was chromatographed on silica eluting with ethyl acetate in DCM and then by preparative HPLC. Fractions containing product were evaporated to give 5-ethoxy-4-hydroxy-1-methyl-3-[1-methyl-5-(trifluoromethyl)pyrazol-3-yl]imidazolidin-2-one (1.61 g, 38%) and 4,5-dihydroxy-1-methyl-3-[1-methyl-5-(trifluoromethyl)pyrazol-3-yl]imidazolidin-2-one (0.79 g, 21%).

5-Ethoxy-4-hydroxy-1-methyl-3-[1-methyl-5-(trifluoromethyl)pyrazol-3-yl]imidazolidin-2-one $^1$H NMR (400 MHz, CDCl$_3$) δ 6.95 (s, 1H), 5.53 (s, 1H), 5.30 (s, 1H), 4.69 (s, 1H), 3.85 (s, 3H), 3.51-3.71 (m, 2H), 2.95 (s, 3H), 1.26 (t, 3H).

LC-MS: positive ES MH+ 309.

4,5-Dihydroxy-1-methyl-3-[1-methyl-5-(trifluoromethyl)pyrazol-3-yl]imidazolidin-2-one Major diastereomer: $^1$H NMR (400 MHz, CDCl$_3$) δ 6.85 (m, 1H), 5.50 (m, 1H), 4.90 (s, 1H), 3.84 (s, 3H), 2.98 (m, 3H).

Minor diastereomer: 6.94 (s, 1H), 5.67 (m, 1H), 5.09 (m, 1H), 3.88 (m, 3H), 2.92 (s, 3H).

LC-MS: positive ES MH+ 281.

Example 4—(5R)-4-hydroxy-1,5-dimethyl-3-[1-methyl-5-(trifluoromethyl)pyrazol-3-yl]imidazolidin-2-one (A15)

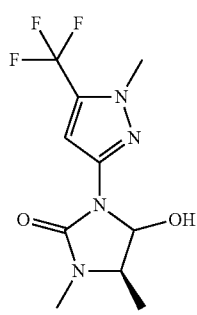 [SMILES: C[C@@H]1C(O)N(c2cc(C(F)(F)F)n(C)n2)C(=O)N1C]

Procedure for Synthesis of (5R)-1,5-dimethyl-3-[1-methyl-5-(trifluoromethyl)pyrazol-3-yl]imidazolidine-2,4-dione (Step-1)

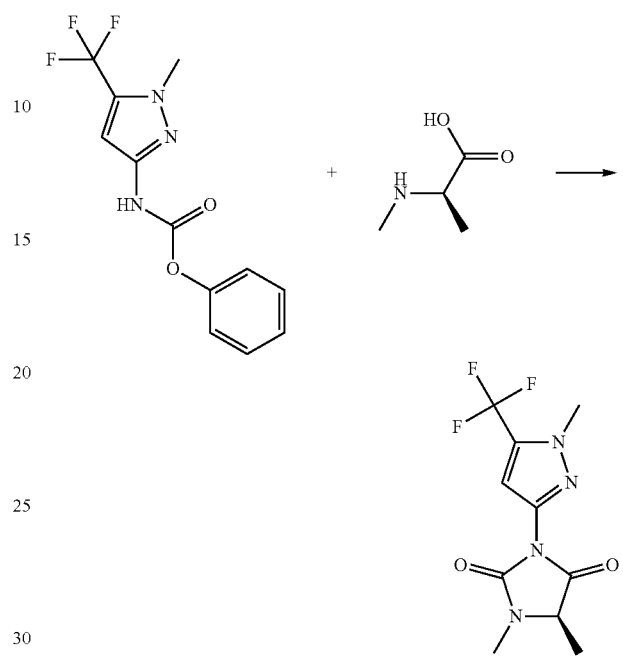

Phenyl N-[1-methyl-5-(trifluoromethyl)pyrazol-3-yl]carbamate (2.5 g, 8.8 mmol) was suspended in acetonitrile (10 mL) under a nitrogen atmosphere and (2R)-2-(methylamino)propanoic acid was added. The reaction was heated in the microwave at 140° C. for 60 mins. The solvent was removed in vacuo and the residue was purified was chromatographed on silica eluting with ethyl acetate in Hexane. Fractions containing product were evaporated to give the desired product, which was used as in the next step without further purification.

LC-MS: (positive ES MH+ 277).

Procedure for Synthesis of (5R)-4-hydroxy-1,5-dimethyl-3-[1-methyl-5-(trifluoromethyl)pyrazol-3-yl]imidazolidin-2-one (A15) (Step-2)

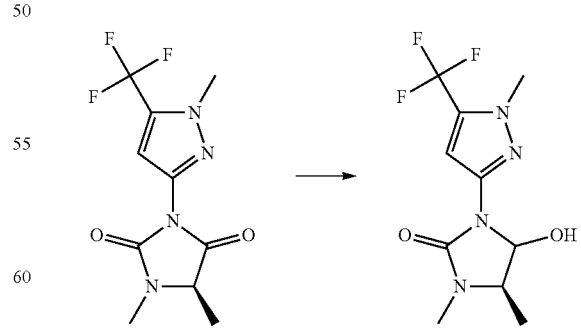

(5R)-1,5-dimethyl-3-[1-methyl-5-(trifluoromethyl)pyrazol-3-yl]imidazolidine-2,4-dione (2 g, 7.24 mmol) was dissolved in methanol (30 mL) and the solution was cooled to around −5° C. (ice-salt bath). NaBH$_4$ (0.280 g 7.24 mmol)

was added in a single portion and the reaction was stirred keeping the temperature between −5° C. and 0° C. for an hour. The mixture was then allowed to warm slowly to +10° C. After approx 3 h, the reaction mixture was quenched by the careful addition of water (1.0 mL). After a few minutes stirring the mixture was diluted further with water (40 mL). The aqueous mixture was extracted with DCM (3×25 mL). The organic extracts were then combined, washed with brine (20 mL), dried over MgSO₄, filtered and the filtrate concentrated giving a white gum (1.304 g, 93%).

¹H NMR: (CDCl₃) and chiral HPLC indicated formation of (5R)-4-hydroxy-1,5-dimethyl-3-[1-methyl-5-(trifluoromethyl)pyrazol-3-yl]imidazolidin-2-one as a mixture of diastereomers. Chiral HPLC indicated ~20% of (5S)-4-hydroxy-1,5-dimethyl-3-[1-methyl-5-(trifluoromethyl)pyrazol-3-yl]imidazolidin-2-one was formed with this procedure also as a mixture of diastereomers.

Less than 5% of (5S)-4-hydroxy-1,5-dimethyl-3-[1-methyl-5-(trifluoromethyl)pyrazol-3-yl]imidazolidin-2-one is formed if phenyl N-[1-methyl-5-(trifluoromethyl)pyrazol-3-yl]carbamate is replaced by (4-nitrophenyl) N-[1-methyl-5-(trifluoromethyl)pyrazol-3-yl]carbamate in step 1. The step 1 reaction then requires lower temperature (80° C. for 1 h).

The stereochemistry of the chiral centre at the carbon containing the R₃ group was generally found to interconvert in solution at room temperature and depending on the nature of R₂ substitution and the conditions for product synthesis, purification and analysis the ratio of diastereromers and position of the —OH group proton may change. This explains the apparent NMR differences between samples A2 and A15.

LC-MS: (positive ES MH+ 279).

Major diastereomer: ¹H NMR (400 MHz, CDCl₃) δ 6.99 (s, 1H), 5.71 (d, 1H), 4.21 (br s, 1H), 3.87 (s, 3H), 3.70 (m, 1H), 2.84 (s, 3H), 1.36 (d, 3H).

Minor diastereomer: 6.99 (s, 1H), 5.38 (d, 1H), 4.40 (br s, 1H), 3.86 (s, 3H), 3.50 (m, 1H), 2.88 (s, 3H), 1.30 (d, 3H).

Example 5—(5S)-4-hydroxy-1,5-dimethyl-3-[1-methyl-5-(trifluoromethyl)pyrazol-3-yl]imidazolidin-2-one (A16)

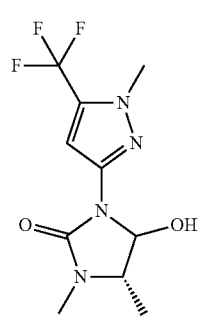 [SMILES: C[C@H]1C(O)N(c2cc(C(F)(F)F)n(C)n2)C(=O)N1C]

Procedure as in example 4 but using (2S)-2-(methylamino)propanoic acid.

Example 6—Preparation of 5-tert-butyl-1-methyl-pyrazol-3-amine for Use in Synthesis of Examples Such as A3, A7, A10

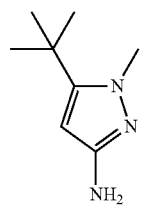

Procedure for Synthesis of (Z)-3-Chloro-4,4-dimethyl-pent-2-enenitrile (Step-1)

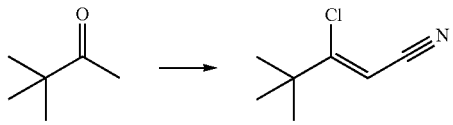

To a three-neck round bottomed flask, equipped with a nitrogen inlet was added dimethylformamide (80 mL, 1000 mmol). The reaction mixture was cooled to 0° C. Phosphorus oxychloride (2.4 equiv, 958.47 mmol) was added dropwise at such a rate to keep temperature below 25° C. with constant stirring with a mechanical stirrer. A solution of 3,3-dimethylbutan-2-one (40 g, 399.36 mmol) in 1,2-dichloroethane (140 mL, 1750 mmol) was added dropwise and reaction was heated at 50-55° C. for 2 h and then at 70-75° C. for another 2 h. Hydroxylamine hydrochloride (2.4 equiv., 958.5 mmol) was added portion wise. Care should be taken for exotherm (temperature rises up to 80° C.). Reaction mixture was then heated to reflux 80° C. for 2 h then cooled down. Water (300 mL) was added to the reaction followed by tert-butyl methyl ether (250 mL). Some sticky material was formed initially which dissolved after stirring for 3-4 h. The organic layer was separated and water layer was again extracted with tert-butyl methyl ether (250 mL×2). Combined organic layers were dried over anhydrous sodium sulfate (and concentrated to give crude material. Distillation at 90-95° C. at 89 mbar pressure furnished product (32 g, 56%) as a colorless liquid.

¹H NMR (400 MHz, CDCl₃) δ 5.55 (s, 1H), 1.22 (s, 9H).

Procedure for Synthesis of of 5-tert-butyl-1-methyl-1H-pyrazol-3-ylamine (Step-2)

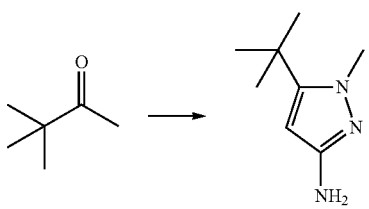

Methylhydrazine sulfate (1.4 g, 10 mmol) was suspended in ethanol (5 mL) to which potassium carbonate (2.76 g, 20 mmol) was added and the reaction was stirred at room temperature for 1 h. A solution of (Z)-3-chloro-4,4-dimethyl-pent-2-enenitrile (1.4 g, 10 mmol) in ethanol (5 mL) was added drop wise to the above reaction mixture and the resultant mixture was heated to reflux for additional 3 h. The reaction was filtered and washed with methanol. The filtrate was concentrated and purified by flash chromatography eluting with ethyl acetate in hexane (0-100%) giving 5-tert-butyl-1-methyl-pyrazol-3-amine (0.830 g, 54%) and also undesired 5-tert-butyl-2-methyl-pyrazol-3-amine (0.200 g, 13%).

$^1$H NMR (400 MHz, CDCl$_3$) δ 5.38 (s, 1H), 3.75 (s, 3H), 1.31 (s, 9H).

Example 7—Preparation of 3-amino-5-tert-butyl-1-methyl-pyrazole-4-carbonitrile for Use in Synthesis of Examples Such as A5, A6

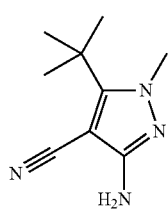

Procedure for Synthesis of 3-amino-5-tert-butyl-1-methyl-pyrazole-4-carbonitrile (Step-1)

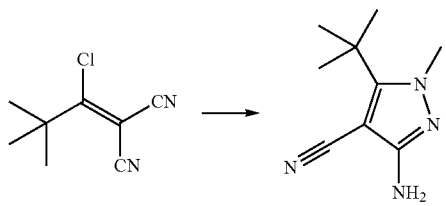

1,8-Diazabicyclo[5.4.0]undec-7-ene (DBU) (3 equiv., 3.558 mmol) and methyl hydrazine sulphate (1.2 equiv., 1.423 mmol) was added into tert-Butanol (21.2 mmol) at room temperature under a Nitrogen atmosphere and stirred for 60 min at room temperature. 2-(1-chloro-2,2-dimethyl-propylidene)propanedinitrile (200 mg, 1.186 mmol) was added in tert-Butanol (21.2 mmol) and the mixture was stirred for 2 h at room temperature. After this time, the reaction mixture was quenched with water (20 mL) and extracted with ethyl acetate (3×50 mL) and the combined organic extracts were dried over Na$_2$SO$_4$ and concentrated under reduced pressure. The desired compound was purified by column chromatography to give the desired product (442 mg, 70%).

Example 8—Preparation of 5-(1-methoxy-1-methyl-ethyl)-1-methyl-pyrazol-3-amine for Use in Synthesis of Examples Such as A18, A19, A20 and A21

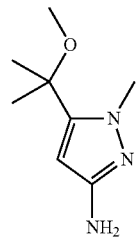

5-(1-methoxy-1-methyl-ethyl)-1-methyl-pyrazol-3-amine was Synthesised According to the Following Scheme

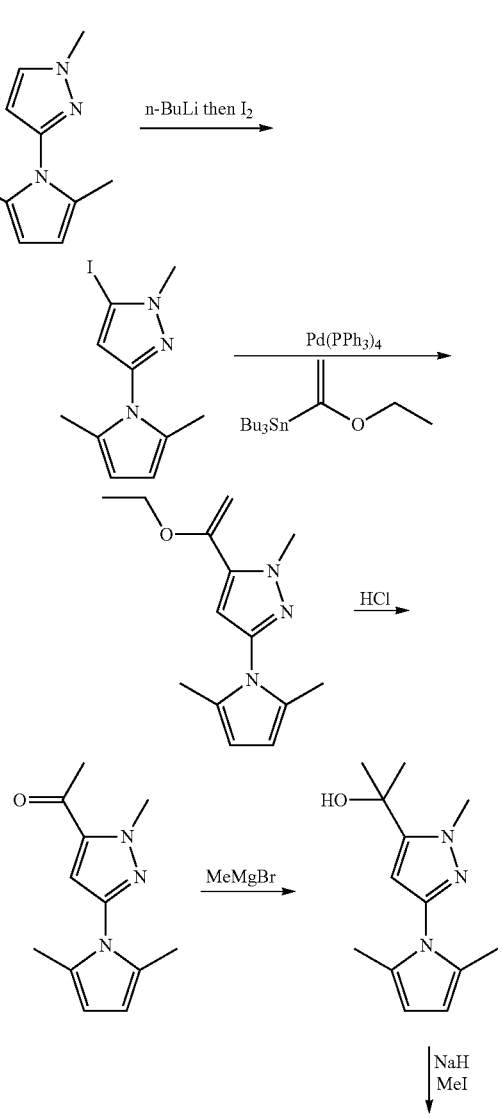

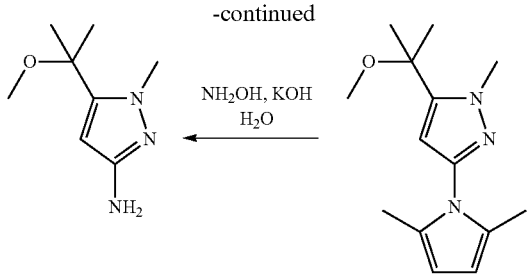

Example 9—Procedure for Synthesis of 1,1,3-trimethoxy-N-methyl-propan-2-amine for Use in Synthesis of Examples Such as A21 and A22

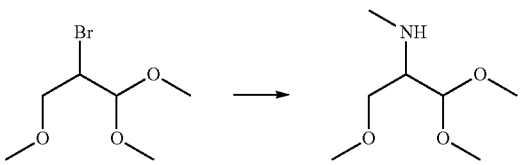

A solution of 2-bromo-1,1,3-trimethoxy-propane (commercially available) (7 g, 32.85 mmol) in methylamine (40% aqueous solution) (105 mL, 210 mmol) was divided into seven equal portions and these were heated at 130° C. for 1 h in a microwave. The combined reaction mixtures were then concentrated and the residue obtained was treated with toluene and evaporated again. The residue was then stirred with DCM, filtered and evaporated to give the crude product that was taken to next step without further purification.

Tables 1 and 2 lists examples of compounds of the general formula (I)

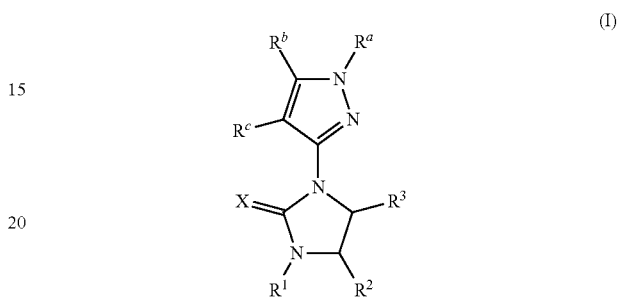

wherein $R^a$, $R^b$, $R^c$, $R^1$, $R^2$, $R^3$ and X are as defined above.

These compounds were made by the general methods described.

TABLE 1

| Compound Number | STRUCTURE | 1H NMR (measured in CDCl$_3$ unless otherwise indicated) δ | LC-MS |
|---|---|---|---|
| A1 | 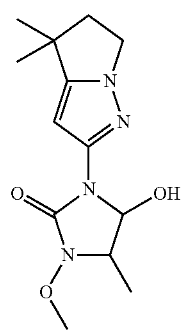 [SMILES: CON1C(=O)N(c2cc3n(n2)CCC3(C)C)C(O)C1C] | Major diastereomer: 6.33 (s, 1H), 5.28 (dd, 1H), 4.72 (brs, 1H), 4.05 (m, 2H), 3.87 (s, 3H), 3.63 (m, 1H), 2.35 (t, 2H), 1.42 (d, 3H) 1.35 (6H, m). Minor diastereomer: 6.31 (s, 1H), 5.58 (dd, 1H), 4.30 (brs, 1H), 4.02 (m, 2H), 3.90 (s, 3H), 3.71 (m, 1H), 2.35 (t, 2H), 1.45 (d, 3H), 1.35 (6H, m). | positive ES MH + 281 |
| A2 | 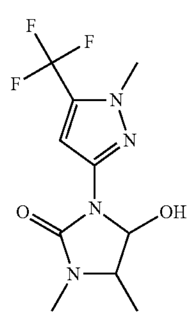 | Major diastereomer: 6.99 (s, 1H), 5.39 (d, 1H), 4.24 (br s, 1H), 3.86 (s, 3H), 3.50 (m, 1H), 2.88 (s, 3H), 1.30 (d, 3H). Minor diastereomer: 6.99 (s, 1H), 5.71 (d, 1H), 4.01 (br s, 1H), 3.86 (s, 3H), 3.70 (m, 1H), 2.83 (s, 3H), 1.36 (d, 3H). | positive ES MH + 281 |

TABLE 1-continued

| Compound Number | STRUCTURE | 1H NMR (measured in CDCl₃ unless otherwise indicated) δ | LC-MS |
|---|---|---|---|
| A3 | 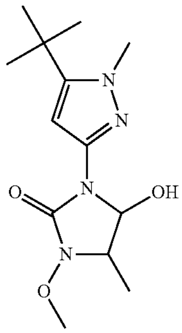 [SMILES: CON1C(=O)N(c2cc(C(C)(C)C)n(C)n2)C(O)C1C] | Major diastereomer: 6.42 (s, 1H), 5.25 (d, 1H), 4.72 (s, 1H), 3.86 (s, 3H), 3.83 (s, 3H), 3.51 (m, 1H), 1.41 (d, 3H), 1.35 (m, 9H). Minor diastereomer: 6.41 (s, 1H), 5.55 (m, 1H), 4.30 (d, 1H) 3.86 (s, 3H), 3.83 (s, 3H), 3.49 (m, 1H), 1.45 (d, 3H), 1.35 (m, 9H). | positive ES MH + 283 |
| A4 | 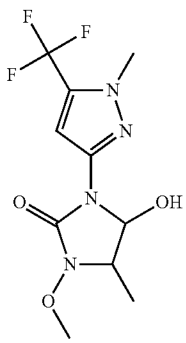 [SMILES: CON1C(=O)N(c2cc(C(F)(F)F)n(C)n2)C(O)C1C] | Major diastereomer): 7.01 (s, 1H), 5.29 (m, 1H), 4.35 (m, 1H), 3.82 (m, 6H), 3.65 (m, 1H), 1.43 (d, 3H). Minor diastereomer): 7.00 (s, 1H), 5.61 (m, 1H), 3.95 (m, 1H), 3.82 (m, 6H), 3.73 (m, 1H), 1.46 (d, 3H). | positive ES MH + 295 |
| A5 | 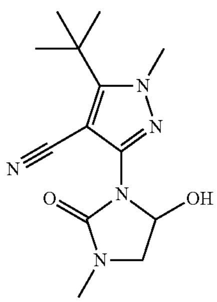 [SMILES: CN1CC(O)N(c2nn(C)c(C(C)(C)C)c2C#N)C1=O] | 5.42 (m, 1H), 4.13 (m, 1H), 4.13 (s, 3H), 3.68 (m, 1H), 3.33 (m, 1H), 2.94 (s, 3H), 1.55 (s, 3H), 1.53 (s, 9H). | positive ES MH + 278 |
| A6 | 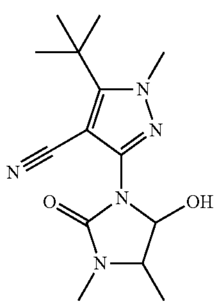 [SMILES: CC1C(O)N(c2nn(C)c(C(C)(C)C)c2C#N)C(=O)N1C] | Major diastereomer: 5.39 (d, 1H), 3.93 (s, 3H), 3.74 (m, 1H), 2.84 (s, 3H), 1.53 (d, 3H), 1.53 (s, 9H). Minor diastereomer: 5.16 (d, 1H), 3.93 (s, 3H), 3.47 (m, 1H), 2.90 (s, 3H), 1.55 (s, 3H) 1.53 (s, 9H). | positive ES MH + 292 |
| A7 | 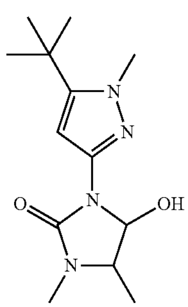 [SMILES: CC1C(O)N(c2cc(C(C)(C)C)n(C)n2)C(=O)N1C] | Major diastereomer: 6.39 (s, 1H), 5.68 (m, 1H), 4.52 (br s, 1H), 3.83 (s, 3H), 3.54 (m, 1H), 2.82 (s, 3H), 1.37 (s, 9H), 1.34 (d, 3H). Minor diastereomer: 6.38 (s, 1H), 5.36 (m, 1H), 4.69 (br s, 1H), 3.84 (s, 3H), 3.45 (m, 1H), 2.86 (s, 3H), 1.37 (s, 9H), 1.28 (d, 3H) | positive ES MH + 265 |

TABLE 1-continued

| Compound Number | STRUCTURE | 1H NMR (measured in CDCl$_3$ unless otherwise indicated) δ | LC-MS |
| --- | --- | --- | --- |
| A8 | 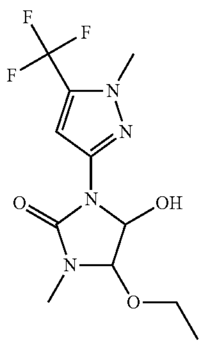 [SMILES: CCOC1C(O)N(c2cc(C(F)(F)F)n(C)n2)C(=O)N1C] | 6.95 (s, 1H), 5.53 (s, 1H), 5.30 (s, 1H), 4.69 (s, 1H), 3.85 (s, 3H), 3.51-3.71 (m, 2H), 2.95 (s, 3H), 1.26 (t, 3H). | positive ES MH + 309 |
| A9 | 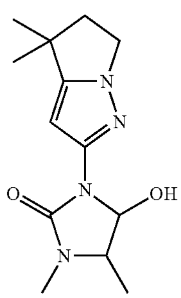 [SMILES: CC1C(O)N(c2cc3n(n2)CCC3(C)C)C(=O)N1C] | Major diastereomer: 6.30 (s, 1H), 5.38 (dd, 1H), 4.85 (br s, 1H), 4.02 (m, 2H), 3.48 (m, 1H), 2.85 (s, 3H), 2.32 (t, 2H), 1.25 (m, 9H). Minor diastereomer: 6.30 (s, 1H), 5.70 (dd, 1H), 4.70 (br s, 1H), 4.12 (m, 2H), 3.65 (m, 1H), 2.85 (s, 3H), 2.32 (t, 2H), 1.25 (m, 9H). | positive ES MH + 265 |
| A10 | 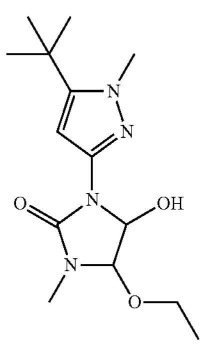 [SMILES: CCOC1C(O)N(c2cc(C(C)(C)C)n(C)n2)C(=O)N1C] | 6.36 (s, 1H), 5.51 (s, 1H), 4.67 (s, 1H), 3.82 (s, 3H), 3.59 (m, 2H), 2.93 (s, 3H), 1.35 (s, 9H), 1.27 (t, 3H). | positive ES MH + 297 |
| A11 | 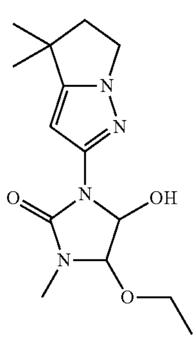 [SMILES: CCOC1C(O)N(c2cc3n(n2)CCC3(C)C)C(=O)N1C] | 6.26 (s, 1H), 5.53 (s, 1H), 4.68 (s, 1H), 4.05 (m, 2H), 3.60 (m, 2H), 2.95 (s, 3H), 2.34 (m, 2H), 1.34 (s, 3H), 1.33 (s, 3H), 1.25 (t, 3H). | positive ES MH + 297 |

TABLE 1-continued

| Compound Number | STRUCTURE | 1H NMR (measured in CDCl₃ unless otherwise indicated) δ | LC-MS |
|---|---|---|---|
| A12 | 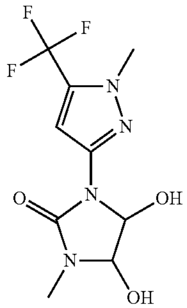 [SMILES: CN1C(=O)N(c2cc(C(F)(F)F)n(C)n2)C(O)C1O] | Major diastereomer: 6.85 (m, 1H), 5.50 (m, 1H), 4.90 (s, 1H), 3.84 (s, 3H), 2.98 (m, 3H). Minor diastereomer: 6.94 (s, 1H), 5.67 (m, 1H), 5.09 (m, 1H), 3.88 (m, 3H), 2.92 (s, 3H). | positive ES MH + 281 |
| A13 | 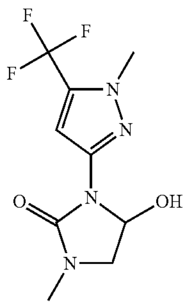 [SMILES: CN1CC(O)N(c2cc(C(F)(F)F)n(C)n2)C1=O] | 6.98 (s, 1H), 5.83 (m, 1H), 4.30 (br s, 1H), 3.87 (s, 3H), 3.66 (dd, 1H), 3.36 (dd, 1H), 2.91 (s, 3H). | positive ES MH + 265 |
| A14 | 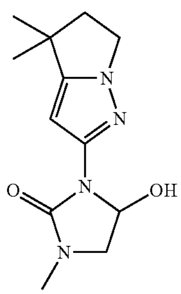 [SMILES: CN1CC(O)N(c2cc3n(n2)CCC3(C)C)C1=O] | 6.29 (s, 1H), 5.82 (dd, 1H) 4.68 (br s, 1H) 3.99 (m, 2H), 3.63 (dd, 1H), 3.34 (dd, 1H), 2.91 (s, 3H) 2.34 (m, 2H) 1.34 (s, 3H) 1.33 (s, 3H). | positive ES MH + 251 |
| A15 | 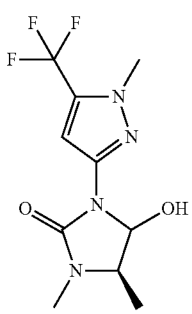 [SMILES: C[C@@H]1C(O)N(c2cc(C(F)(F)F)n(C)n2)C(=O)N1C] | Major diastereomer: 6.99 (s, 1H), 5.71 (d, 1H), 4.21 (br s, 1H), 3.87 (s, 3H), 3.70 (m, 1H), 2.84 (s, 3H), 1.36 (d, 3H). Minor diastereomer: 6.99 (s, 1H), 5.38 (d, 1H), 4.40 (br s, 1H), 3.86 (s, 3H), 3.50 (m, 1H), 2.88 (s, 3H), 1.30 (d, 3H). | positive ES MH + 279 |
| A16 | 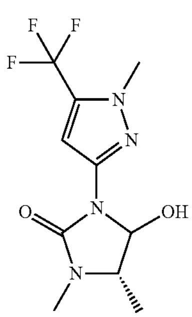 [SMILES: C[C@H]1C(O)N(c2cc(C(F)(F)F)n(C)n2)C(=O)N1C] | As for A15 | As for A15 |

TABLE 1-continued

| Compound Number | STRUCTURE | 1H NMR (measured in CDCl₃ unless otherwise indicated) δ | LC-MS |
|---|---|---|---|
| A17 | 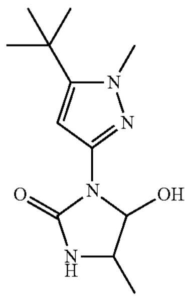 [SMILES: CC1NC(=O)N(c2cc(C(C)(C)C)n(C)n2)C1O] | Major diastereomer: 6.38 (s, 1H), 5.43 (d, 1H), 4.82 (br s, 1H), 4.63 (d, 1H), 3.84 (s, 1H), 3.66 (m, 1H), 1.38 (s, 9H), 1.31 (d, 3H). Minor diastereomer: 6.35 (s, 1H), 5.72 (d, 1H), 4.70 (br s, 1H), 4.51 (d, 1H), 3.98 (s, 1H), 3.85 (m, 1H), 1.38 (s, 9H), 1.34 (d, 3H). | positive ES MH + 253 |
| A18 | 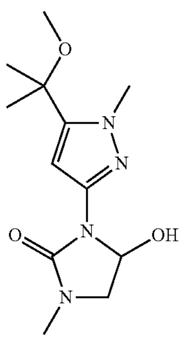 [SMILES: COC(C)(C)c1cc(N2C(=O)N(C)CC2O)nn1C] | 6.47 (s, 1H), 5.82 (dd, 1H), 3.88 (s, 3H), 3.64 (dd, 1H), 3.35 (dd, 1H), 3.09 (s, 3H), 2.91 (s, 3H), 1.57 (s, 3H), 1.56 (s, 3H). | positive ES MH + 269 |
| A19 | 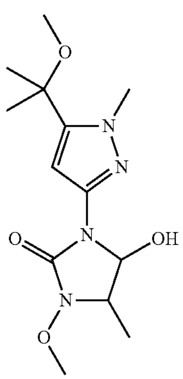 [SMILES: CON1C(=O)N(c2cc(C(C)(C)OC)n(C)n2)C(O)C1C] | Major diastereomer: 6.53 (s, 1H), 5.31 (d, 1H), 3.92 (s, 3H), 3.87 (s, 3H), 3.64 (m, 1H), 3.09 (s, 3H), 1.57 (s, 3H), 1.56 (s, 3H), 1.43 (d, 3H). Minor diastereomer: 6.53 (s, 1H), 5.63 (d, 1H), 3.94 (s, 3H), 3.90 (s, 3H), 3.73 (m, 1H), 3.09 (s, 3H), 1.57 (s, 3H), 1.56 (s, 3H), 1.45 (d, 3H). | positive ES MH + 299 |
| A20 | 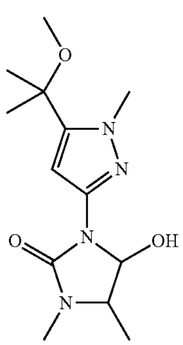 [SMILES: COC(C)(C)c1cc(N2C(=O)N(C)C(C)C2O)nn1C] | Major diastereomer: 6.53 (s, 1H), 5.41 (d, 1H), 3.93 (s, 3H), 3.49 (m, 1H), 3.10 (s, 3H), 2.88 (s, 3H), 1.57 (s, 3H), 1.56 (s, 3H), 1.31 (d, 3H). Minor diastereomer: 6.56 (s, 1H), 5.77 (d, 1H), 3.95 (s, 3H), 3.71 (m, 1H), 3.10 (s, 3H), 2.84 (s, 3H), 1.57 (s, 3H), 1.56 (s, 3H), 1.36 (d, 3H). | positive ES MH + 283 |

TABLE 1-continued

| Compound Number | STRUCTURE | 1H NMR (measured in CDCl₃ unless otherwise indicated) δ | LC-MS |
|---|---|---|---|
| A21 | 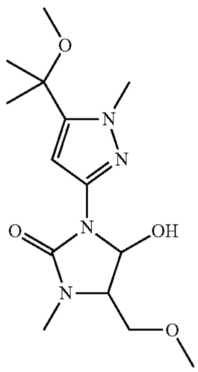 [SMILES: COCC1C(O)N(c2cc(C(C)(C)OC)n(C)n2)C(=O)N1C] | 6.47 (s, 1H), 5.57 (s, 1H), 3.86 (s, 3H), 3.53 (m, 3H), 3.38 (s, 3H), 3.07 (s, 3H), 2.93 (s, 3H), 1.55 (s, 3H), 1.54 (s, 3H). | positive ES MH + 313 |
| A22 | 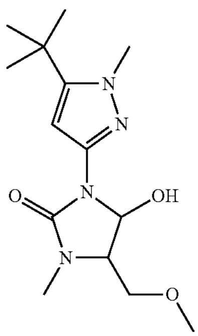 [SMILES: COCC1C(O)N(c2cc(C(C)(C)C)n(C)n2)C(=O)N1C] | 6.39 (s, 1H), 5.56 (s, 1H), 4.68 (s, 1H), 3.84 (s, 3H), 3.52 (m, 3H), 3.38 (s, 3H), 2.93 (s, 3H), 1.37 (s, 9H). | positive ES MH + 297 |

Example 10—Herbicidal Action

Example 10a: Pre-Emergence Herbicidal Activity

Seeds of a variety of test species were sown in standard soil in pots. After cultivation for one day (pre-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Table 2.

TABLE 2

Application pre-emergence

| Compound Number | Rate (g/Ha) | ABUTH | AMARE | ECHCG | SETFA | ALOMY | ZEAMX |
|---|---|---|---|---|---|---|---|
| A1 | 1000 | 5 | 5 | 5 | 4 | 4 | 3 |
| A2 | 1000 | 5 | 5 | 4 | 4 | 4 | 4 |
| A3 | 1000 | 5 | 5 | 4 | 4 | 4 | 3 |
| A4 | 1000 | 5 | 5 | 4 | 4 | 4 | 3 |
| A5 | 1000 | 2 | 4 | 0 | 0 | 1 | 0 |
| A6 | 1000 | 5 | 2 | 2 | 2 | 1 | 1 |
| A7 | 1000 | 4 | 5 | 4 | 5 | 4 | 2 |
| A8 | 1000 | 5 | 5 | 5 | 4 | 4 | 2 |
| A10 | 1000 | 5 | 5 | 5 | 4 | 4 | 2 |
| A12 | 1000 | 5 | 5 | 4 | 4 | 4 | 1 |
| A13 | 1000 | 5 | 5 | 5 | 4 | 4 | 2 |
| A14 | 1000 | 5 | 5 | 4 | 4 | 4 | 3 |
| A15 | 1000 | 5 | 5 | 2 | 3 | 2 | 1 |
| A17 | 1000 | 4 | 5 | 4 | 3 | 3 | 1 |
| A18 | 1000 | 5 | 5 | 4 | 4 | | 2 |
| A19 | 1000 | 5 | 5 | 4 | 4 | | 2 |
| A20 | 1000 | 5 | 5 | 4 | 4 | | 2 |
| A21 | 1000 | 5 | 5 | 4 | 4 | | 2 |
| A22 | 1000 | 5 | 5 | 1 | 1 | 2 | 0 |

Example 10b: Post-Emergence Herbicidal Activity

Seeds of a variety of test species were sown in standard soil in pots. After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Table 3.

TABLE 3

Application post-emergence

| Example number | Rate (g/Ha) | ABUTH | SETFA | AMARE | ECHCG | ZEAMX | ALOMY |
|---|---|---|---|---|---|---|---|
| A1 | 1000 | 5 | 5 | 5 | 5 | 5 | 4 |
| A2 | 1000 | 5 | 5 | 5 | 5 | 4 | 5 |
| A3 | 1000 | 5 | 5 | 5 | 5 | 4 | 5 |
| A4 | 1000 | 5 | 5 | 5 | 5 | 5 | 5 |
| A5 | 1000 | 4 | 3 | 5 | 3 | 2 | 3 |
| A6 | 1000 | 5 | 5 | 5 | 4 | 2 | 4 |
| A7 | 1000 | 5 | 5 | 5 | 5 | 4 | 4 |
| A8 | 1000 | 5 | 5 | 5 | 5 | 4 | 5 |
| A10 | 1000 | 5 | 5 | 5 | 5 | 5 | 5 |
| A12 | 1000 | 5 | 5 | 5 | 5 | 4 | 5 |
| A13 | 1000 | 5 | 5 | 5 | 5 | 4 | 5 |
| A14 | 1000 | 5 | 5 | 5 | 5 | 5 | 5 |
| A15 | 1000 | 5 | 5 | 5 | 5 | 5 | 5 |
| A17 | 1000 | 4 | 2 | 4 | 3 | 0 | 3 |
| A18 | 1000 | 5 | 5 | 5 | 4 | 2 | |
| A19 | 1000 | 5 | 5 | 5 | 5 | 3 | |
| A20 | 1000 | 5 | 4 | 5 | 5 | 3 | |
| A21 | 1000 | 5 | 4 | 5 | 3 | 2 | |
| A22 | 1000 | 5 | 5 | 5 | 5 | 4 | |

ABUTH = *Abutilon theophrasti*;; AMARE = *Amaranthus retroflexus*; SETFA = *Setaria faberi*; ALOMY = *Alopecurus myosuroides*; ECHCG = *Echinochloa crus-galli*; ZEAMX = *Zea mays*.

The invention claimed is:
1. A compound of formula (I)
wherein

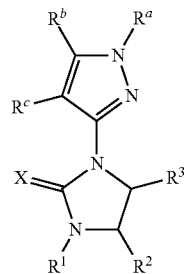

(I)

X is selected from S and O;
$R^a$ is selected from hydrogen, $C_1$-$C_6$ alkyl and $C_1$-$C_6$ haloalkyl;
$R^b$ is selected from hydrogen, formyl, hydroxyl, halogen, nitro, cyano, $C_1$-$C_6$ alkyl, $C_1$-$C_6$ cyanoalkyl, $C_3$-$C_6$ cycloalkyl, $C_3$-$C_6$ cyanocycloalkyl, $C_1$-$C_6$ haloalkyl, $C_1$-$C_6$ alkylthio, $C_1$-$C_6$ alkoxy, $C_1$-$C_6$ alkoxy $C_1$-$C_6$ alkyl, $C_1$-$C_6$ alkylthio $C_1$-$C_6$ alkyl, $C_1$-$C_6$ cyanoalkoxy, $C_1$-$C_6$ haloalkoxy, $C_1$-$C_6$ alkoxy $C_1$-$C_6$ alkoxy, $C_2$-$C_6$ alkenyl, $C_2$-$C_6$ alkynyl, $C_2$-$C_6$ cyanoalkenyl, $C_2$-$C_6$ cyanoalkynyl, $C_2$-$C_6$ alkenyloxy, $C_2$-$C_6$ alkynyloxy, $C_2$-$C_6$ haloalkenyl, $C_2$-$C_6$ haloalkynyl, $C_2$-$C_6$ haloalkenyloxy, $C_2$-$C_6$ haloalkynyloxy, $C_1$-$C_6$ alkoxy $C_2$-$C_6$ alkenyl, $C_1$-$C_6$ alkoxy $C_2$-$C_6$ alkynyl, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylsulfonyloxy, $C_1$-$C_6$ alkylcarbonyl, $C_1$-$C_6$ haloalkylcarbonyl, $C_2$-$C_6$ alkenylcarbonyl, $C_2$-$C_6$ alkynylcarbonyl, $C_2$-$C_6$ haloalkenylcarbonyl, $C_2$-$C_6$ haloalkynylcarbonyl, tri $C_1$-$C_6$ alkylsilyl $C_2$-$C_6$ alkynyl, a group $R^5R^6N$—, a group $R^5C(O)N(R^6)$—, a group $R^5R^6NC(O)$—, a group $R^5S(O_2)N(R^6)$—, a group $R^5R^6NSO_2$—, a $C_6$-$C_{10}$ aryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ aryloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ benzyl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ benzyloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_3$-$C_6$ heterocyclyl group optionally substituted by from 1 to 3 groups independently selected from $C_1$-$C_4$ alkyl and a $C_3$-$C_6$ cycloalkyl group optionally substituted with from 1 to 3 groups independently selected from halogen or $C_1$-$C_6$ alkyl;
$R^c$ is selected from hydrogen, halogen, cyano, $C_1$-$C_6$ alkyl and $C_1$-$C_6$ haloalkyl;
or $R^a$ and $R^b$ together with the nitrogen and carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl;

or $R^b$ and $R^c$ together with the carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl;

$R^1$ is selected from hydrogen, $C_1$-$C_4$ alkyl, $C_1$-$C_4$ alkoxy and $C_1$-$C_4$ haloalkyl;

$R^2$ is selected from hydrogen, hydroxyl, $C_1$-$C_4$ alkyl, $C_1$-$C_4$ alkoxy, $C_1$-$C_4$ alkoxy-$C_1$-$C_4$ alkyl, $C_1$-$C_4$ haloalkyl, $C_1$-$C_3$ haloalkoxy and $C_1$-$C_4$ cyanoalkyl;

or $R^1$ and $R^2$ together with the nitrogen and carbon atoms to which they are attached form a 3-7 membered saturated or partially unsaturated ring optionally comprising from 1 to 3 heteroatoms independently selected from S, O and N and optionally substituted with from 1 to 3 groups independently selected from hydroxyl, =O, $C_1$-$C_6$ alkyl or $C_1$-$C_6$ haloalkyl;

$R^3$ is selected from halogen, hydroxyl, $-NR^{10}R^{11}$ and any one of the following groups

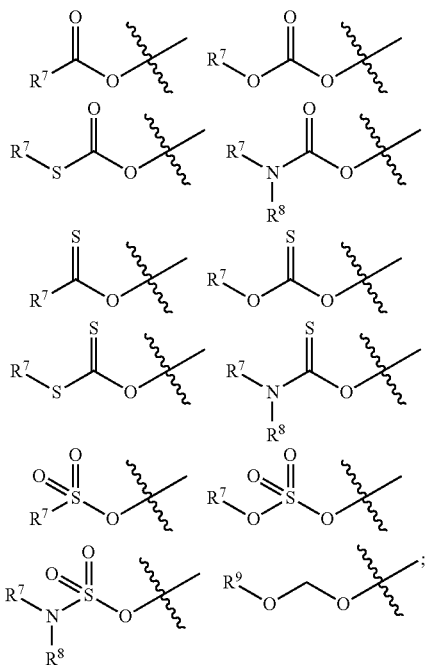

$R^5$ and $R^6$ are independently selected from hydrogen, $C_1$-$C_6$ alkyl, $C_1$-$C_6$ haloalkyl, $C_2$-$C_6$ alkenyl and $C_2$-$C_6$ alkynyl;

$R^7$ and $R^8$ are independently selected from hydrogen, $C_1$-$C_6$ alkyl, $C_1$-$C_6$ haloalkyl, $C_2$-$C_6$ alkenyl, $C_2$-$C_6$ alkynyl, a $C_5$-$C_{10}$ heteroaryl group which can be mono- or bicyclic comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy and a $C_6$-$C_{10}$ aryl group optionally substituted with 1 to 3 groups independently selected from halogen, nitro, cyano, $C_1$-$C_3$ alkyl, $C_1$-$C_3$ or $R^7$ and $R^8$ together with the atoms to alkoxy, $C_1$-$C_3$ haloalkyl and $C_1$-$C_3$ haloalkoxy, or $R^7$ and $R^8$ together with the atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;

$R^9$ is selected from $C_1$-$C_6$ alkyl and benzyl optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy; and $R^{10}$ and $R^{11}$ are, independently, selected from hydrogen, $C_1$-$C_{20}$ alkyl, $C_1$-$C_{20}$ haloalkyl, $C_2$-$C_{20}$ alkenyl and $C_2$-$C_{20}$ alkynyl.

2. The compound of claim 1, wherein X is O.

3. The compound of claim 1, wherein $R^a$ is selected from hydrogen, methyl and ethyl or $R^a$ and $R^b$ together with the nitrogen and carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl.

4. The compound of claim 1, wherein $R^b$ is selected from hydrogen, halogen, $C_1$-$C_6$ alkyl, $C_3$-$C_6$ cycloalkyl, $C_1$-$C_6$ haloalkyl, $C_2$-$C_5$ alkenyl, a $C_6$-$C_{10}$ aryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy and a $C_3$-$C_6$ heteroaryl group optionally substituted by from 1 to 3 groups independently selected from $C_1$-$C_4$ alkyl, or $R^a$ and $R^b$ together with the nitrogen and carbon atoms to which they are attached form a 3-7 membered saturated or partially unsaturated ring optionally comprising 1 to 3 heteroatoms independently selected from S, O and N and optionally substituted with 1 to 3 groups independently selected from $C_1$-$C_6$ alkyl or $R^b$ and $R^c$ together with the carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl.

5. The compound of claim 4, wherein $R^b$ is selected from hydrogen, halogen, $C_1$-$C_4$ alkyl, $C_1$-$C_4$ haloalkyl, $C_2$-$C_4$ alkenyl and $C_1$-$C_4$ alkoxy.

6. The compound of claim 1, wherein $R^c$ is selected from hydrogen, methyl and cyano or $R^b$ and $R^c$ together with the carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl.

7. The compound of claim 1, wherein $R^1$ is selected from $C_1$-$C_4$ alkyl, $C_1$-$C_4$ alkoxy and $C_1$-$C_4$ haloalkyl.

8. The compound of claim 1, wherein $R^2$ is selected from hydrogen, hydroxyl, $C_1$-$C_3$ alkyl, $C_1$-$C_3$ alkoxy and $C_1$-$C_3$ alkoxy-$C_1$-$C_3$ alkyl.

9. The compound of claim 1, wherein $R^3$ is selected from hydroxyl, halogen, $C_1$-$C_6$ alkylcarbonyloxy, $C_1$-$C_6$ alkoxycarbonyloxy and $C^6$-$C^{10}$ aryloxycarbonyloxy wherein the aryl group may be substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy.

10. The compound of claim 1, wherein X is O, $R^1$ is selected from hydrogen, $C_1$-$C_3$ alkyl and $C_1$-$C_3$ alkoxy, $R^2$ is selected from hydrogen, hydroxyl, $C_1$-$C_3$ alkyl, $C_1$-$C_3$ alkoxy and $C_1$-$C_3$ alkoxy-$C_1$-$C_3$ alkyl, $R^3$ is hydroxyl, $R^a$ is $C_1$-$C_3$ alkyl, $R^b$ is selected from $C_1$-$C_4$ alkyl and $C_1$-$C_3$ haloalkyl or $R^a$ and $R^b$ together with the nitrogen and carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl and $R^c$ is selected from hydrogen and cyano.

11. A herbicidal composition comprising a compound of formula I as defined in claim 1 together with at least one agriculturally acceptable adjuvant or diluent.

12. A composition according to claim 11 further comprising an herbicide in addition to the compound of formula I.

13. A composition according to claim 11 further comprising a safener.

14. A method of controlling weeds in crops of useful plants, comprising applying to said weeds or to the locus of said weeds, or to said useful plants or to the locus of said useful plants, a compound of formula I as defined in claim 1.

* * * * *